US007305850B2

(12) United States Patent
Tonkovich et al.

(10) Patent No.: US 7,305,850 B2
(45) Date of Patent: Dec. 11, 2007

(54) DISTILLATION PROCESS USING MICROCHANNEL TECHNOLOGY

(75) Inventors: Anna Lee Tonkovich, Marysville, OH (US); Wayne W. Simmons, Dublin, OH (US); Laura J. Silva, Dublin, OH (US); Dongming Qiu, Dublin, OH (US); Steven T. Perry, Galloway, OH (US); Thomas Yuschak, Dublin, OH (US)

(73) Assignee: Velocys, Inc., Plain City, OH (US)

( * ) Notice: Subject to any disclaimer, the term of this patent is extended or adjusted under 35 U.S.C. 154(b) by 339 days.

(21) Appl. No.: 10/898,687

(22) Filed: Jul. 23, 2004

(65) Prior Publication Data

US 2006/0016215 A1 Jan. 26, 2006

(51) Int. Cl.
*F25J 3/00* (2006.01)

(52) U.S. Cl. .................. 62/617; 62/623; 62/643; 62/902

(58) Field of Classification Search .................. 62/617, 62/643, 623, 903, 902, 905
See application file for complete search history.

(56) References Cited

U.S. PATENT DOCUMENTS

| | | | |
|---|---|---|---|
| 3,477,917 A | 11/1969 | Rodgers | 203/10 |
| 3,562,116 A | 2/1971 | Rodgers | 202/200 |
| 3,661,721 A | 5/1972 | Rodgers | 202/172 |
| 4,392,362 A | 7/1983 | Little | 62/514 |
| 4,516,632 A | 5/1985 | Swift et al. | 165/167 |
| 4,597,947 A * | 7/1986 | Almaula | 422/191 |
| 5,309,637 A | 5/1994 | Moriarty | 29/890.054 |
| 5,317,805 A | 6/1994 | Hoopman et al. | 29/890.03 |

(Continued)

FOREIGN PATENT DOCUMENTS

CN 1068973 2/1993

(Continued)

OTHER PUBLICATIONS

Besser, Ronald S. "New Directions in Reactor Design Through Miniaturization". Sep. 13, 2002, Tulane Engineering Forum.

(Continued)

*Primary Examiner*—William C Doerrler
(74) *Attorney, Agent, or Firm*—Renner, Otto, Boisselle & Sklar, LLP

(57) ABSTRACT

The disclosed invention relates to a process for distilling a fluid mixture in a microchannel distillation unit, the microchannel distillation unit comprising a plurality of microchannel distillation sections, the fluid mixture comprising a more volatile component and a less volatile component, the process comprising: flowing a vapor phase of the fluid mixture in a first microchannel distillation section in contact with a liquid phase of the fluid mixture, part of the more volatile component transferring from the liquid phase to the vapor phase to form a more volatile component rich vapor phase, part of the less volatile component transferring from the vapor phase to the liquid phase to form a less volatile component rich liquid phase; separating the more volatile component rich vapor phase from the less volatile component rich liquid phase; flowing the less volatile component rich liquid phase to another microchannel distillation section upstream from the first microchannel distillation section; and flowing the more volatile rich vapor phase to another microchannel distillation section downstream from the first microchannel distillation section.

91 Claims, 9 Drawing Sheets

U.S. PATENT DOCUMENTS

| | | | |
|---|---|---|---|
| 5,611,214 A | 3/1997 | Wegeng et al. | 62/498 |
| 5,727,618 A | 3/1998 | Mundinger et al. | 165/80.4 |
| 5,811,062 A | 9/1998 | Wegeng et al. | 422/129 |
| 5,858,314 A | 1/1999 | Hsu et al. | 422/211 |
| 6,126,723 A * | 10/2000 | Drost et al. | 96/4 |
| 6,129,973 A | 10/2000 | Martin et al. | 428/166 |
| 6,192,596 B1 | 2/2001 | Bennett et al. | 34/76 |
| 6,200,536 B1 | 3/2001 | Tonkovich et al. | 422/177 |
| 6,216,343 B1 | 4/2001 | Leland et al. | 29/890.032 |
| 6,220,497 B1 | 4/2001 | Benz et al. | 228/118 |
| 6,230,408 B1 | 5/2001 | Ehrfeld et al. | 29/890.039 |
| 6,313,393 B1 | 11/2001 | Drost | 136/201 |
| 6,352,577 B1 | 3/2002 | Martin et al. | 96/4 |
| 6,381,846 B2 | 5/2002 | Insley et al. | 29/890.039 |
| 6,415,860 B1 | 7/2002 | Kelly et al. | 165/748 |
| 6,488,838 B1 | 12/2002 | Tonkovich et al. | 208/108 |
| 6,540,975 B2 | 4/2003 | Tonkovich et al. | 423/659 |
| 6,666,909 B1 * | 12/2003 | TeGrotenhuis et al. | 95/273 |
| 6,675,875 B1 | 1/2004 | Vafai et al. | 165/80.4 |
| 6,746,819 B1 | 6/2004 | Schmitz et al. | 430/272.1 |
| 6,747,178 B1 | 6/2004 | Harston et al. | 570/175 |
| 6,749,814 B1 | 6/2004 | Bergh et al. | 422/130 |
| 6,749,817 B1 | 6/2004 | Mulvaney, III | 422/200 |
| 6,755,211 B1 | 6/2004 | O'Connor et al. | 137/554 |
| 6,769,444 B2 | 8/2004 | Guzman et al. | 137/15.01 |
| 6,770,245 B2 | 8/2004 | Akporiaye et al. | 422/82.12 |
| 6,773,684 B2 | 8/2004 | Lesieur et al. | 422/198 |
| 6,875,247 B2 * | 4/2005 | TeGrotenhuis et al. | 55/319 |
| 6,912,864 B2 * | 7/2005 | Roche et al. | 62/256 |
| 7,051,540 B2 * | 5/2006 | TeGrotenhuis et al. | 62/93 |
| 7,220,388 B2 | 5/2007 | Bishop et al. | 422/100 |
| 2002/0144600 A1 | 10/2002 | TeGrotenhuis et al. | 95/273 |
| 2004/0104010 A1 | 6/2004 | Kenny et al. | 165/80.4 |
| 2004/0123626 A1 | 7/2004 | Caze et al. | 65/17.2 |
| 2004/0125689 A1 | 7/2004 | Ehrfeld et al. | 366/165.1 |
| 2004/0130057 A1 | 7/2004 | Mehrabi et al. | 264/171.13 |
| 2004/0131346 A1 | 7/2004 | Kylberg et al. | 392/465 |
| 2004/0131507 A1 | 7/2004 | Saitmacher et al. | 422/111 |
| 2004/0131829 A1 | 7/2004 | Joseph et al. | 428/166 |
| 2004/0136902 A1 | 7/2004 | Plath et al. | 423/651 |
| 2004/0141893 A1 | 7/2004 | Martin | 422/198 |
| 2004/0143059 A1 | 7/2004 | Cabrera | 524/800 |
| 2004/0144421 A1 | 7/2004 | Parce et al. | 137/14 |
| 2004/0156762 A1 | 8/2004 | Schuppich et al. | 422/191 |
| 2004/0234566 A1 * | 11/2004 | Qiu et al. | 424/401 |
| 2007/0241066 A1 | 10/2007 | Bishop et al. | 210/774 |

FOREIGN PATENT DOCUMENTS

| | | |
|---|---|---|
| DE | 19812067 | 10/1999 |
| EP | 1 311 341 B1 | 8/2001 |
| EP | 1 362 634 A1 | 11/2003 |
| WO | 97/32687 | 9/1997 |
| WO | 98/55812 | 12/1998 |
| WO | 00/06295 | 2/2000 |
| WO | 01/10773 A1 | 2/2001 |
| WO | 01/12312 A2 | 2/2001 |
| WO | 01/54807 A1 | 2/2001 |
| WO | 0 904 608 B1 | 12/2001 |
| WO | 01/95237 A2 | 12/2001 |
| WO | 03/026788 | 4/2003 |
| WO | 03/078052 A1 | 9/2003 |
| WO | 03/106386 A2 | 12/2003 |
| WO | 2004/045760 | 6/2004 |
| WO | 2004/050799 | 6/2004 |
| WO | 2004/052518 | 6/2004 |
| WO | 2004/052530 | 6/2004 |
| WO | 2004/052941 | 6/2004 |
| WO | 2004/054013 | 6/2004 |
| WO | 2004/054696 | 7/2004 |
| WO | 2004/062790 | 7/2004 |
| WO | 2004/062791 | 7/2004 |
| WO | 2004/062792 | 7/2004 |
| WO | 2004/067160 | 8/2004 |
| WO | 2004/067444 | 8/2004 |
| WO | 2004/067708 | 8/2004 |

OTHER PUBLICATIONS

Ouyang et al. "Flexible Microreactor System for Chemical Research at Moderate and High Temperatures". Stevens Institute of Technology.

Matlosz et al.; "Microreactors as Tools in Chemical Research"; Microreaction Technology; IMRET 5: Proceedings of the Fifth International Conference on Microreaction Technology.

Srinivasn et al.; "Micromachined Reactors for Catalytic Partial Oxidation Reactions"; AIChE Journal; Nov. 1997; vol. 43, No. 11; pp. 3059-3069.

TeGrotenhuis et al.; Optimizing Microchannel Reactors by Trading-Off Equilibrium and Reaction Kinetics through Temperature Management; Prepared for presentation at IMRET 6-6th International Conference on Microreaction Technology; Mar. 2002.

Wegeng et al.; "Compact Fuel Processors for Fuel Cell Powered Automobiles Based on Microchannel Technology"; Fuel Cells Bulletin No. 28; pp. 8-13.

Rostami et al.; "Flow and Heat Transfer for Gas Flowing in Microchannels: a Review"; Heat and Mass Transfer 38 (2002) 359-367.

TeGrotenhuis et al.; "Normal Gravity Testing of a Microchannel Phase Separator for Insitu Resource Utiliization"; NASA/CR-2001-210955.

"Modular Micro Chemical Engineering: Micro Distillation Column"; Micro ChemTec.

Aguirre et al.; Optimal Thermodynamic Approximation to Reversible Distillation by Means of Interheaters and Intercoolers; Ind. Eng. Chem. Res. 1997, 36, 4882-4893.

Benedict; Multistage Separation Process; *Transactions American Institute Chemical Engineers*; vol. 43, No. 2, pp. 41-60, Feb. 1947.

Invitation to Pay Additional Fees and Partial International Search Report, Application No. PCT/US2005/024444, mailed Jan. 19, 2006.

International Preliminary Report on Patentability, Application No. PCT/US2005/024444, Mailed Dec. 1, 2006.

* cited by examiner

DISTILLATION PROCESS USING MICROCHANNEL TECHNOLOGY

TECHNICAL FIELD

This invention relates to a distillation process for separating two or more components having different volatilities from a liquid mixture containing the components. The process employs microchannel technology for effecting the distillation and is particularly suitable for conducting difficult separations, such as the separation of ethane from ethylene, wherein the individual components are characterized by having volatilities that are very close to one another.

BACKGROUND

Distillation is a method of separation that is based on the difference in composition between a liquid mixture and the vapor formed from it. This composition difference arises from the dissimilar effective vapor pressures, or volatilities, of the components of the liquid mixture. Distillation as normally practiced involves condensation of the vaporized material, usually in multiple vaporization/condensation sections.

Distillation is a widely used industrial method for separating liquid mixtures and is at the heart of the separation processes in many chemical and petroleum plants. The most elementary form of the method is simple distillation in which the liquid is brought to boiling and the vapor formed is separated and condensed to form a product. If the process is continuous it is called flash distillation. If the feed mixture is available as an isolated batch of material the process is a form of batch distillation and the compositions of the collected vapor and residual liquid are thus time dependent. The term fractional distillation, which may be contracted to fractionation, was originally applied to the collection of separate fractions of condensed vapor, each fraction being segregated. In modern practice the term is applied to distillation processes in general, where an effort is made to separate an original mixture into two or more streams, at least one of which is enriched in at least one component. When the vapors are enriched by contact with counter-flowing liquid reflux, the process is often called rectification. When fractional distillation is accomplished with a continuous feed of material and continuous removal of product fractions, the process is called continuous distillation. When steam is added to the vapors to reduce the partial pressures of the components to be separated, the term steam distillation is used.

Most distillations conducted commercially operate continuously, with a more volatile fraction recovered as distillate and a less volatile fraction recovered as bottoms or residue. If a portion of the distillate is condensed and returned to the process to enrich the vapors, the liquid is called reflux. The apparatus in which the enrichment occurs is usually a vertical, cylindrical vessel called a still or distillation column. This apparatus normally contains internal devices for effecting vapor-liquid contact; the devices may be categorized as plates or packings.

A problem with many distillation processes is that they employ relatively large pieces of equipment that are highly inefficient with respect to energy consumption. Distillation accounts for about a quadrillion BTUs of energy consumption per year in the United States. Conventional distillation systems could reduce lost work and increase plant energy efficiency by incorporating capital-intensive reboilers at multiple sections. However, the capital cost of adding multiple reboilers to conventional distillation columns is typically prohibitive. The trade-off between energy and capital often results in favoring the lower cost solution. The efficiency of mass transfer sections in distillation columns is set by the effectiveness of trays or packing, which has not changed significantly in many years. For separation of components with similar boiling points, such as separating ethane from ethylene, commercial distillation columns are typically hundreds of feet high, due to the need to use many mass transfer sections.

Another problem relates to the fact that the equipment (e.g., distillation columns, reboilers, condensers, etc.) used in many of these distillation processes require relatively large internal volumes for processing the materials being treated. These large internal volumes render the equipment slow to respond to changes in operating conditions (e.g., temperature, etc.). This makes the distillation processes using this equipment slow to start up and subject to imprecise control.

SUMMARY

The present invention provides a solution to these problems by employing a distillation process using microchannel technology. With the present invention, in one embodiment, process intensification is achieved through the use of stacked layers of thin sheets of material with stamped or etched channels, that is, microchannels, providing narrow flow paths with short diffusion distances for mass transfer. The use of these microchannels can provide for dramatic reductions in the required flow length of the section dominated by mass transfer, resulting in relatively short distillation units. Heat inputs and outputs can be closely integrated with microchannel vapor-liquid equilibrium stages resulting in processes that can approach reversible distillation.

This invention relates to a process for distilling a fluid mixture in a microchannel distillation unit, the microchannel distillation unit comprising a plurality of microchannel distillation sections, the fluid mixture comprising a more volatile component and a less volatile component, the process comprising: flowing a vapor phase of the fluid mixture in a first microchannel distillation section in contact with a liquid phase of the fluid mixture, part of the more volatile component transferring from the liquid phase to the vapor phase to form a more volatile component rich vapor phase, part of the less volatile component transferring from the vapor phase to the liquid phase to form a less volatile component rich liquid phase; separating the more volatile component rich vapor phase from the less volatile component rich liquid phase; flowing the less volatile component rich liquid phase to another microchannel distillation section upstream from the first microchannel distillation section; and flowing the more volatile rich vapor phase to another microchannel distillation section downstream from the first microchannel distillation section.

In one embodiment, each microchannel distillation section comprises at least one process microchannel and at least one adjacent liquid channel, the liquid channel comprising a wicking region.

In one embodiment, the microchannel distillation unit further comprises a heat exchanger.

In one embodiment, for each microchannel distillation section the process microchannel comprises a liquid inlet for permitting liquid to flow into the process microchannel, a liquid outlet for permitting liquid to flow out of the process microchannel, an interior wall extending from the liquid inlet to the liquid outlet, and a capture structure, the liquid inlet being downstream from the liquid outlet. In one embodiment, the liquid phase flows along the interior wall, the liquid phase being in the form of a thin film.

In one embodiment, part of the wicking region forms a wall of the process microchannel.

In one embodiment, the liquid phase flows in the wicking region and the vapor phase flows in the process microchannel and contacts at least part of the liquid phase in the wicking region.

In one embodiment, the more volatile component rich vapor phase is a first section more volatile component rich vapor phase formed in the first microchannel distillation section of the process microchannel, the process microchannel comprising the first microchannel distillation section and downstream second and third microchannel distillation sections, the first section more volatile component rich vapor phase flowing from the first microchannel distillation section into the downstream second microchannel distillation section, a downstream third section less volatile component rich liquid phase formed in the downstream third microchannel distillation section flowing from the downstream third microchannel distillation section into the downstream second microchannel distillation section and contacting the first section more volatile component rich vapor phase in the downstream second microchannel distillation section, the downstream third section less volatile component rich liquid phase flowing in a thin film along an interior wall in the downstream second microchannel distillation section, part of the more volatile component transferring from the downstream third section less volatile component rich liquid phase to the first section more volatile component rich vapor phase to form a downstream second section more volatile component rich vapor phase, part of the less volatile component transferring from the first section more volatile component rich vapor phase to the downstream third section less volatile component rich liquid phase to form a downstream second section less volatile component rich liquid phase; and separating the downstream second section more volatile component rich vapor phase from the downstream second section less volatile component rich liquid phase.

In one embodiment, the less volatile component rich liquid phase is a first section less volatile component rich liquid phase formed in the first microchannel distillation section of the process microchannel, the process microchannel comprising the first microchannel distillation section and upstream second and third microchannel distillation sections, the first section less volatile component rich liquid phase flowing from the first microchannel distillation section into the upstream second microchannel distillation section, an upstream third section more volatile component rich vapor phase formed in the upstream third microchannel distillation section flowing from the upstream third microchannel distillation section into the upstream second microchannel distillation section and contacting the first section less volatile component rich liquid phase in the upstream second microchannel distillation section, the first section less volatile component rich liquid phase flowing in a thin film along an interior wall in the upstream second microchannel distillation section, part of the more volatile component transferring from first section less volatile component rich liquid phase to the upstream third section more volatile component rich vapor phase to form an upstream second section more volatile component rich vapor phase, part of the less volatile component transferring from the upstream third section more volatile component rich vapor phase to the first section less volatile component rich liquid phase to form an upstream second section less volatile component rich liquid phase; and separating the upstream second section more volatile component rich vapor phase from the upstream second section less volatile component rich liquid phase.

In one embodiment, each microchannel distillation section further comprises a heat exchange channel adjacent to the liquid channel, the process microchannel, or both the liquid channel and the process microchannel.

In one embodiment, the microchannel distillation unit further comprises a first supplemental vapor channel and a second supplemental vapor channel, each microchannel distillation section further comprising a supplemental vapor inlet and a supplemental vapor outlet, part of the vapor phase flowing from the first supplemental vapor channel through the supplemental vapor inlet into the microchannel distillation section, through the microchannel distillation section in contact with the liquid phase, and then through the supplemental vapor outlet to the second supplemental vapor channel.

In one embodiment, each microchannel distillation section comprises a liquid channel, a first process microchannel, a second process microchannel, a first vapor channel, a second vapor channel, a third vapor channel, a vapor inlet and a vapor outlet, the first process microchannel and the second process microchannel being adjacent to the liquid channel, the liquid channel comprising a wicking region, part of the wicking region forming a wall of the first process microchannel and a wall of the second process microchannel; the liquid phase flowing through the wicking region; the vapor phase flowing through the vapor inlet into the first vapor channel, through the first vapor channel into the first process microchannel, through the first process microchannel in contact with at least part of the liquid phase in the wicking region, from the first process microchannel into the second vapor channel, through the second vapor channel into the second process microchannel, through the second process microchannel in contact with at least part of the liquid phase in the wicking region, from the second process microchannel into the third vapor channel, and through the third vapor channel into the vapor outlet.

In one embodiment, the invention relates to a process for distilling a fluid mixture in a microchannel distillation unit, the microchannel distillation unit comprising a process microchannel and an adjacent liquid channel, the fluid mixture comprising a more volatile component and a less volatile component, the process comprising: flowing a vapor phase of the fluid mixture in one direction through the process microchannel, the process microchannel comprising a plurality of microchannel distillation sections, each microchannel distillation section comprising an interior space for permitting vapor flow, an interior wall, a capture structure, a liquid inlet and a liquid outlet, the capture structure and the liquid outlet being downstream from the liquid inlet, the interior wall extending from the liquid inlet to the liquid outlet, the capture structure being suitable for capturing liquid and permitting vapor to flow through it, the liquid outlet being suitable for permitting the flow of liquid from the capture structure through the liquid outlet into the liquid channel, the liquid inlet being suitable for permitting liquid to flow from the liquid channel into the process microchannel; flowing a liquid phase of the fluid mixture through the liquid channel in a direction opposite to the direction of flow of the vapor phase in the process microchannel, the liquid channel including a wicking region, the liquid phase flowing through the wicking region; the liquid phase flowing from the liquid channel through the liquid inlet in a first microchannel distillation section of the process microchannel and flowing as a thin film along the interior wall to the capture structure within the first microchannel distillation section, the vapor phase flowing through the first microchannel distillation section in contact with the liquid phase flowing along the interior wall, part of the more volatile component transferring from the liquid phase to the vapor phase to form a more volatile component rich vapor phase, part of the less volatile component transferring from the vapor phase to the liquid phase to form a less volatile component rich liquid phase, the less volatile component rich liquid phase contacting the capture structure and flowing from the capture structure through the liquid outlet of the first microchannel distillation section into the liquid channel, the more volatile component rich vapor phase flowing through the capture structure of the first microchannel distillation section.

In one embodiment, the invention relates to a process for separating ethylene from a fluid mixture comprising ethylene and ethane in a distillation unit comprising a plurality of microchannel distillation sections, the process comprising: contacting a vapor phase of the fluid mixture with a liquid phase of the fluid mixture in each of the microchannel distillation sections, progressively enriching the vapor phase with ethylene to form an ethylene enriched vapor phase, and separating the ethylene enriched vapor phase from the distillation unit, the distillation unit having a height of up to about 20 meters, the separated ethylene enriched vapor phase having an ethylene content of at least about 95% by volume.

In one embodiment, the invention relates to a process for distilling a fluid mixture in a distillation apparatus comprising a plurality of microchannel distillation units, each microchannel distillation unit comprising a plurality of microchannel distillation sections, the fluid mixture comprising a more volatile component and a less volatile component, the process comprising: flowing a vapor phase of the fluid mixture in a first microchannel distillation section of at least one of the microchannel distillation units in contact with a liquid phase of the fluid mixture, part of the more volatile component transferring from the liquid phase to the vapor phase to form a more volatile component rich vapor phase, part of the less volatile component transferring from the vapor phase to the liquid phase to form a less volatile component rich liquid phase; separating the more volatile component rich vapor phase from the less volatile component rich liquid phase; flowing the less volatile component rich liquid phase to another microchannel distillation section in the microchannel distillation unit upstream from the first microchannel distillation section; and flowing the more volatile rich vapor phase to another microchannel distillation section in the microchannel distillation unit downstream from the first microchannel distillation section. In one embodiment, the distillation process is conducted in all of the microchannel distillation units in the distillation apparatus. In one embodiment, the distillation process is conducted in some but not all of the microchannel distillation units in the distillation apparatus.

In one embodiment, the invention relates to a microchannel distillation unit, comprising: a process microchannel and a liquid channel; the liquid channel being adjacent to the process microchannel, the liquid channel comprising a wicking region; the process microchannel comprising a plurality of microchannel distillation sections, each microchannel distillation section comprising an internal space for permitting vapor flow, an interior wall for permitting liquid to flow as a thin film along the interior wall, a capture structure for capturing liquid and permitting vapor to flow through it, a liquid outlet for permitting liquid to flow from the capture structure into the liquid channel, and a liquid inlet for permitting liquid to flow from the liquid channel into the process microchannel.

In one embodiment, the invention relates to a microchannel distillation unit, comprising: a liquid channel, a first process microchannel, a second process microchannel, a first vapor channel, a second vapor channel, a third vapor channel, a vapor inlet and a vapor outlet, the first process microchannel and the second process microchannel being adjacent to the liquid channel, the liquid channel comprising a wicking region, part of the wicking region forming a wall of the first process microchannel and a wall of the second process microchannel, the first vapor channel being adjacent to the first process microchannel, the third vapor channel being adjacent to the second process microchannel, the second vapor channel being adjacent to the first and third vapor channels, the first and third vapor channels being positioned between the first and second process microchannels and the second vapor channel.

BRIEF DESCRIPTION OF THE DRAWINGS

In the annexed drawings, like parts and features have like designations.

DETAILED DESCRIPTION

The term "microchannel" refers to a channel having at least one internal dimension of height or width of up to about 10 millimeters (mm), and in one embodiment up to about 5 mm, and in one embodiment up to about 2 mm, and in one embodiment up to about 1 mm. In one embodiment, the height or width is in the range of about 0.01 to about 10 mm, and in one embodiment about 0.05 to about 5 mm, and in one embodiment about 0.05 to about 2 mm, and in one embodiment about 0.05 to about 1.5 mm, and in one embodiment about 0.05 to about 1 mm, and in one embodiment about 0.05 to about 0.75 mm, and in one embodiment about 0.05 to about 0.5 mm. Both height and width are perpendicular to the direction of flow through the microchannel.

The term "adjacent" when referring to the position of one channel relative to the position of another channel means directly adjacent. In one embodiment, a wall may separate the two channels, in part or in whole. This wall may vary in thickness. In one embodiment, a process microchannel and a liquid channel may be in fluid contact with one another. For example, a process microchannel may have an opening exposed to the wicking region of a liquid channel. However, "adjacent" channels are not separated by an intervening channel that would interfere with heat transfer between the channels.

Figure 10:
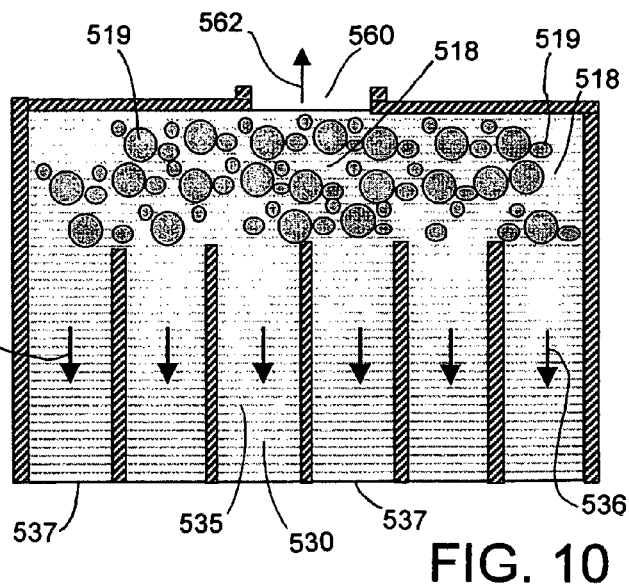
FIG. 10 is a schematic illustration of the microchannel condenser illustrated in FIG. 9 taken along line I-I in FIG. 9.

The terms "upstream" and "downstream" refer to positions within the process microchannels used in the inventive process that are relative to the direction of flow of the vapor phase through the process microchannels. For example, a position within the process microchannels not yet reached by a portion of the vapor phase flowing toward that position would be downstream of that portion of the vapor phase. A position within the process microchannels already passed by a portion of the vapor phase flowing away from that position would be upstream of that portion of the vapor phase. The upstream and downstream positions for the microdistillation unit illustrated in FIG. 10 are relative to the direction of flow of the vapor phase in the vapor channels 540 and 540a. The terms "upstream" and "downstream" do not necessarily refer to a vertical position since the process microchannels used in the inventive process may be oriented horizontally, vertically or at an inclined angle.

The term "capture structure" refers to a structure positioned within a channel that captures liquid and permits vapor to flow through it.

The term "wick" refers to medium for drawing off liquid by capillary action.

The term "wicking region" refers to a space occupied by a wick and/or a wicking surface (e.g., a grooved surface).

The term "fluid" refers to a gas, a liquid, or a gas or a liquid containing dispersed solids, or a mixture thereof. The fluid may be in the form of a liquid containing dispersed liquid droplets. The fluid may be in the form of a gas containing dispersed liquid droplets.

Figure 1:
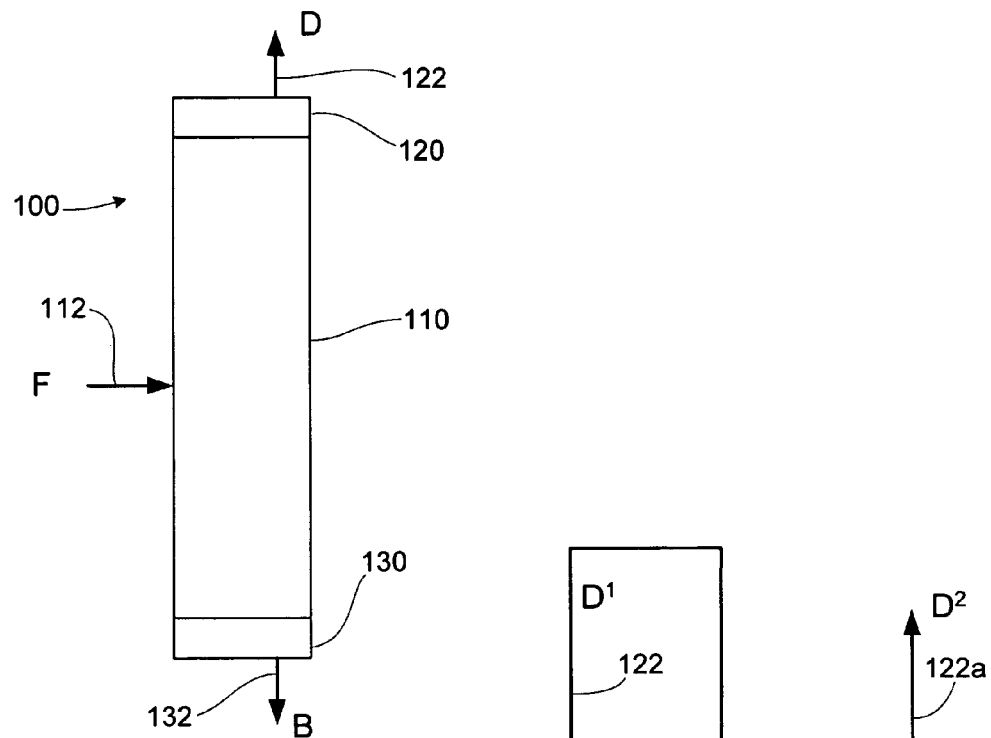
FIG. 1 is a flow sheet illustrating a distillation process that can be used in accordance with the inventive process.

The inventive process will be described initially with reference to FIG. 1. Referring to FIG. 1, a distillation process 100 is provided for distilling a fluid mixture containing components X and Y. Component Y is more volatile than component X. The distillation process 100 employs microchannel distillation column or apparatus 110, which includes microchannel condenser 120, and microchannel reboiler 130. The distillation column or apparatus 110 contains one or more of the inventive microchannel distillation units which are provided for separating component X from component Y. Each of the microchannel distillation units comprises a plurality of microchannel distillation sections. In operation, a feed F comprising a fluid mixture comprising components X and Y enters distillation column or apparatus 110, as indicated by arrow 112. Within the distillation column or apparatus 110 a vapor phase flows through a series of microchannel distillation sections in a direction towards the microchannel condenser 120 and a liquid phase flows through a series of microchannel distillation sections in a direction towards the microchannel reboiler 130. In each microchannel distillation section the vapor phase and the liquid phase contact each other with the result being a mass transfer between the phases. In each microchannel distillation section part of the more volatile component Y transfers from the liquid phase to the vapor phase, and part of the less volatile component X transfers from the vapor phase to the liquid phase. The vapor phase, which is progressively enriched with the more volatile component Y, flows through distillation column or apparatus 110 towards the microchannel condenser 120 and into the microchannel condenser 120. The liquid phase, which is progressively enriched with the less volatile component X, flows through the distillation column 100 towards the microchannel reboiler 130 and into the microchannel reboiler 130. The vapor phase is condensed in the microchannel condenser 120 to form distillate product D. Part of the distillate product D, which may be referred to as an overhead product (sometimes called a head or a make), may be withdrawn from the system, as indicated by arrow 122. Part of the distillate product D may be returned to the distillation column or apparatus 110 where it flows through the distillation column in the form of a liquid phase. The liquid phase, in the form of bottoms product B, flows into the microchannel reboiler 130. Part of the bottoms product B may be withdrawn from the system, as indicated by arrow 132. Part of the bottoms product may be vaporized in the microchannel reboiler 130 and returned to the distillation column or apparatus 110 where it flows through the distillation column or apparatus 110 in the form of a vapor phase. The ratio between the amount of distillate product D that is removed from the system and the amount that is returned to the system may be referred to as the reflux ratio. The ratio between the amount of bottoms product B that is removed from the system and the amount that is returned to the system may be referred to as the boil-up ratio. These ratios can vary and can be determined by those skilled in the art.

Figure 2:
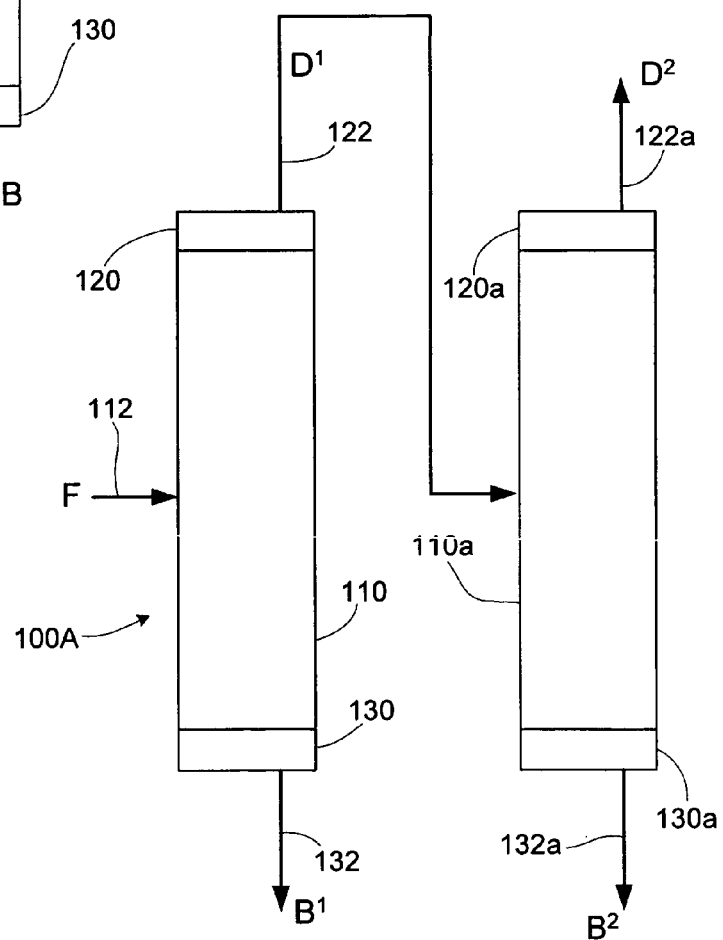
FIG. 2 is a flow sheet illustrating an alternate embodiment of a distillation process that can be used in accordance with the inventive process.

The distillation process 100A illustrated in FIG. 2 is also suitable for conducting the inventive process. The distillation process 100A is similar to the distillation process 100 with the exception that the distillation process 100A is suitable for effecting separation between three components, namely, components X, Y and Z, from a feed F comprising components X, Y and Z. Components Y and Z are more volatile than component X, and component Z is more volatile than component Y. Distillation process 100A employs two distillation columns or apparatus, namely, distillation columns or apparatus 110 and 110a. Distillation columns or apparatus 110 and 110a in FIG. 2 function in the same manner as distillation column or apparatus 110 in FIG. 1. The feed F containing components X, Y and Z flows into distillation column or apparatus 110, as indicated by line 112. A mixture enriched with component X is separated as first bottoms product $B^1$. Part of the first bottoms product $B^1$ can be recirculated back through distillation column or apparatus 110 in the same manner as discussed above for distillation column or apparatus 110 in FIG. 1. The remainder of the first bottoms product $B^1$ is withdrawn from the system, as indicated by arrow 132. A mixture enriched with components Y and Z is separated as a first distillate product $D^1$. Part of the first distillate product $D^1$ can be recirculated back through distillation column or apparatus 110 in the same manner as discussed above for distillation column or apparatus 110 in FIG. 1. The remainder of the first distillate product $D^1$ flows to distillation column or apparatus 110a, as indicated by line 122, wherein a second distillate product $D^2$ enriched with component Z is withdrawn from the distillation column or apparatus 110a, as indicated by line 122a. A second bottoms product $B^2$ containing an enriched concentration of component Y is withdrawn from distillation column or apparatus 110a, as indicated by line 132a. The second distillate product $D^2$ and second bottoms product $B^2$ can be partially recirculated back through the distillation column or apparatus 110a in the same manner as discussed above for distillation column or apparatus 110 in FIG. 1.

In addition to the distillation processes illustrated in FIGS. 1 and 2, there are other distillation processes that are known for separating fluids for which the inventive microchannel distillation process may be employed. These include: partitioned columns; topping and tailing processes or tailing and topping processes, which employ two distillation columns; easiest separation first processes, which employ three distillation columns; and full thermal coupling processes which employ two distillation columns. These distillation processes are described in Becker et al., "The World's Largest Partitioned Column with Trays—Experiences from Conceptual Development to Successful Start-Up," Reports on Science and Technology 62/2000, pages 42-48. The microchannel distillation units used with the inventive process can be employed in these distillation processes. An advantage of using the inventive microchannel distillation units is that the distillation systems that employ the inventive microchannel distillation units can be built on smaller scales that consume significantly less energy and still produce the same level of product output as conventional distillation systems. Another advantage of using the inventive microchannel distillation units relates to the ability to closely space partitions within these microchannel distillation units or to closely space thermally coupled streams by integration of such thermally coupled streams with adjacent channels or within adjacent or nearly adjacent layers in the same microchannel distillation unit. The close spacing of the thermally coupled streams may reduce one or more of thermal response times, control feedback times, and start-up times needed for achieving steady-state operations for continuous distillation processes.

Figure 3:
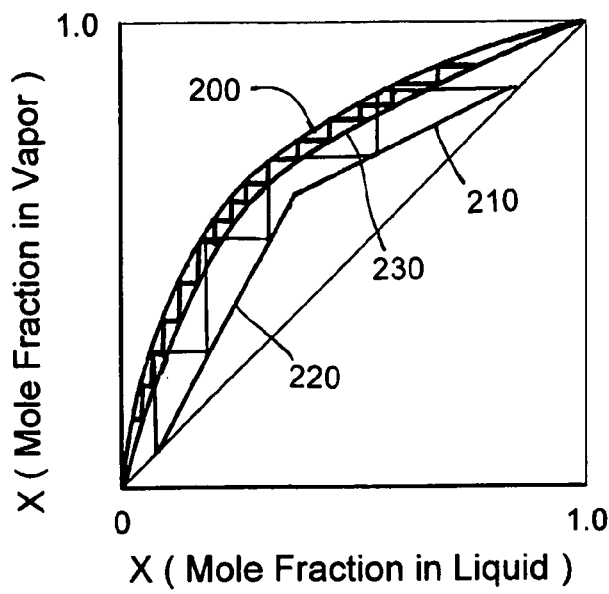
FIG. 3 is a drawing illustrating the McCabe-Thiele graphical method for calculating the number of distillation sections for a distillation process.

As is well known in the art, the number of theoretical sections for effecting a desired separation for two components in a distillation process may be calculated using the McCabe-Thiele graphical method which is illustrated in FIG. 3. Referring to FIG. 3, an equilibrium line 200 for the vapor phase and the liquid phase of component X is plotted. The operating lines 210 and 220 for a conventional distillation process are depicted in FIG. 3 for purposes of comparison. Line 210 would be the rectifying operating line while line 220 would be the stripping operating line. The number of theoretical stages required for the distillation can be calculated using the horizontal and vertical lines extending from the rectifying line 210 and stripping line 220 to the equilibrium curve 200. Operating line 230 which is also shown in FIG. 3 would correspond to an operating line which more closely approaches a reversible distillation process. A process following operating line 230 would not be economical using conventional technology due to the prohibitive cost of adding separation sections and heat exchangers. While no chemical process is reversible in a thermodynamic sense, and entropy always increases, an advantage of the inventive process is that reversible distillation can be closely approached. With the inventive process, the difference in temperature between the vapor and liquid phases in each section can be minimized. A longitudinal temperature profile in the distillation column or apparatus can be imposed by external heating or cooling via a thermally conducting column housing heat exchange channels adjacent to some or all the microchannel distillation sections. This makes it possible to achieve a temperature profile that is very close to the equilibrium line 200 shown in FIG. 3.

The heat exchange channels may impose tailored temperature profiles for individual microchannel distillation sections or groups of microchannel distillation sections. Computational design methods for multi-component fractionations are known in the art and may be applied to this invention where heat exchange channels are used to create a close approach to equilibrium.

The height to an equivalent theoretical plate (HETP) ratio is well known in the art for calculating the mass transfer efficiency of hardware for effecting vapor-liquid contacting processes. In conventional distillation processes, the HETP is typically on the order of about 2 feet (about 61 cm) for trays and packing. On the other hand, with the inventive process the HETP may be less than about 1 foot (about 30.5 cm), and in one embodiment less than about 1 inch (about 2.54 cm), and in one embodiment in the range from about 0.01 to about 1 cm. This provides the inventive process with the advantage of employing more theoretical distillation stages in a more compact system than conventional processes and yet achieve similar separation and product throughput results. For example, for the separation of ethane from ethylene in the production of >99% by volume pure ethylene, the distillation column or apparatus used with the inventive process may be less than about 20 meters (about 65 feet), and in one embodiment less than about 3 meters (about 9.8 feet), while with conventional processes the same separation would require a distillation column that would be hundreds of feet high.

Figure 4:
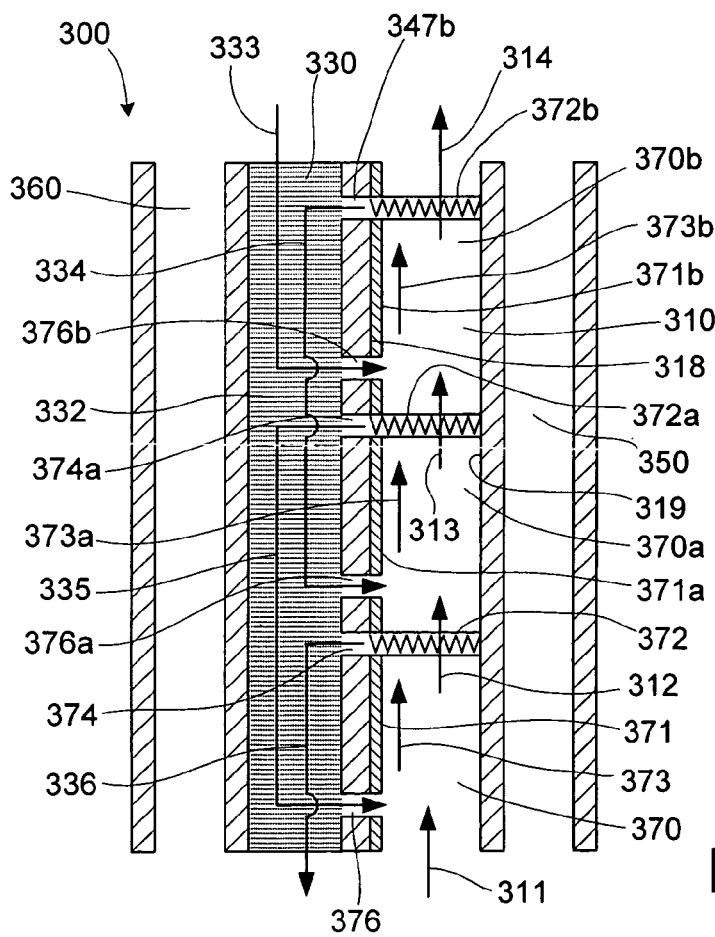
FIG. 4 is a schematic illustration of a microchannel distillation unit that can be used in accordance with the inventive process.

The microchannel distillation unit that may be used in the inventive distillation process, which includes processes employing the above-described distillation columns, including distillation columns 110 and 110A, in one embodiment, may have the construction illustrated in FIG. 4. Referring to FIG. 4, microchannel distillation unit 300 comprises process microchannel 310, liquid channel 330, and heat exchange channels 350 and 360. Liquid channel 330 is adjacent to process microchannel 310. Heat exchange channel 350 is adjacent to process microchannel 310, and heat exchange channel 360 is adjacent to liquid channel 330. It will be understood that if the microchannel distillation unit 300 is repeated in a microchannel distillation column or apparauts, each repetition of the microchannel distillation unit 300 may share a heat exchange channel with the next adjacent microchannel distillation unit 300, thus each repetition of the microchannel distillation unit 300 may have one heat exchange channel rather than two heat exchange channels. For example, the heat exchange channel 350 of one microchannel distillation unit 300 may also function as the heat exchange channel 360 of the next adjacent microchannel distillation unit 300. Alternatively, a heat exchange channel may be placed adjacent to or near two or more microchannel distillation units 300, for example two, three, four, five, six, etc., microchannel distillation units, and thereby provide the desired heat exchange requirements for such microchannel distillation units.

The illustrated embodiment depicted in FIG. 4 contains three microchannel distillation sections, namely, microchannel distillation sections 370, 370a, and 370b. It will be understood, however, that the microdistillation unit 300 may comprise any desired number of microchannel distillation sections, for example, four, five, six, eight, ten, tens, hundreds, thousands, etc. Each of the microchannel distillation sections comprises an interior wall (371, 371a, 371b), a capture structure (372, 372a, 372b), a liquid outlet (374, 374a, 374b), and a liquid inlet (376, 376a, 376b). The interior wall (371, 371a, 371b) may function as a wetted wall. The capture structures (372, 372a, 372b) and the liquid exits (374, 374a, 374b) are adjacent to each other and are suitable for permitting the flow of liquid from the process microchannel 310 to the liquid channel 330. The liquid inlets (376, 376a, 376b) are positioned upstream from the liquid outlets (374, 374a, 374b) and are suitable for permitting liquid to flow from the liquid channel 330 into the process microchannel 310. The liquid channel 330 comprises a wicking region 332. The wicking region 332 comprises a wick and/or a wicking surface. The wicking region 332 includes flow passages (e.g., grooves) which allow liquid to flow through the wicking region from the liquid exit (for example, liquid outlet 374b) of each microchannel distillation section to the liquid entrance (for example, liquid inlet 376a) of the next adjacent upstream microchannel distillation section.

In operation, a liquid phase containing components X and Y flows through flow passages in the wicking region 332 in the liquid channel 330. The flow of the liquid phase may be driven by gravitational force and/or a pressure differential. The pressure differential may be effected by a pump, a suction device, or other apparatus or techniques known in the art. In one embodiment, a combination of gravitational force and pumping may be used. The liquid phase flows from the wicking region 332 through liquid inlet 376b, as indicated by arrow 333. The liquid phase enters microchannel distillation section 370b and flows along interior wall 371b as a thin film, as indicated by arrow 373b, until it contacts capture structure 372b. A vapor phase containing components X and Y flows through capture structure 372a into microchannel distillation section 370b, as indicated by arrow 313, and flows through microchannel distillation section 370b until it contacts capture structure 372b. The flow of the liquid phase along the interior wall 371b may be driven by gravity, capillary force and/or drag from the flow of the vapor phase through the microchannel distillation section 370b. In the microchannel distillation section 370b the liquid phase and the vapor phase contact each other. Part of the more volatile component Y transfers from the liquid phase to the vapor phase to form a component Y rich vapor phase. Part of the less volatile component X transfers from the vapor phase to the liquid phase to form a component X rich liquid phase. The vapor phase flows through capture structure 372b, as indicated by arrow 314. The liquid phase flows from capture structure 372b through liquid outlet 374b. The flow of the liquid phase through the liquid exit 374b may be as a result of capillary force. The liquid phase flows through flow passages in the wicking region 332, as indicated by arrow 334, and then through liquid inlet 376a. The flow of the liquid phase through the liquid inlet 376a may be driven by gravitational force, a pressure differential as a result of the flow of the vapor phase near the liquid inlet 376a, and/or a wetting effect resulting from the flow of the liquid phase along the interior wall (371, 371a, 371b). The liquid phase flowing through liquid inlet 376a enters microchannel distillation section 370a and flows along interior wall 371a as a thin film, as indicated by arrow 373a, until it contacts capture structure 372a. The vapor phase flows through capture structure 372 into microchannel distillation section 370a, as indicated by arrow 312, and flows through microchannel distillation section 370a until it contacts capture structure 372a. The vapor phase flow may be driven by a pressure differential. Within microchannel section 370a, the liquid phase and the vapor phase contact each other. Part of the more volatile component Y transfers from the liquid phase to the vapor phase to form a component Y rich vapor phase. Part of the less volatile component X transfers from the vapor phase to the liquid phase to form a component X rich liquid phase. The vapor phase flows through capture structure 372a into microchannel distillation section 370b, as indicated by arrow 313. The liquid phase flows from capture structure 372a through liquid outlet 374a through flow passages in the wicking region 332 in liquid channel 330, as indicated by arrow 335, into liquid inlet 376. The liquid phase flows through liquid inlet 376 into microchannel distillation section 370 and along interior wall 371 as a thin film, as indicated by arrow 373, until it contacts capture structure 372. The vapor phase flows into microchannel distillation section 370, as indicated by arrow 311, and flows through microchannel distillation section 370 until it contacts capture structure 372. Within the microchannel distillation section 370 the liquid phase and the vapor phase contact each other. Part of the more volatile component Y transfers from the liquid phase to the vapor phase to form a component Y rich vapor phase. Part of the less volatile component X transfers from the vapor phase to the liquid phase to form a component X rich liquid phase. The component X rich liquid phase flows from capture structure 372 through liquid outlet 374 into liquid channel 330, as indicated by arrow 336. The liquid phase flowing along line 336 has a higher concentration of component X and a lower concentration of component Y than the liquid phase flowing downwardly through liquid channel 330 into liquid inlet 376b, as indicated by arrow 333. The vapor phase flowing through capture structure 372b, as indicated by arrow 314, has a higher concentration of component Y and a lower concentration of component X than the vapor phase entering microchannel distillation section 370, as indicated by arrow 311. Within the liquid channel 330 the more volatile component Y may vaporize and form vapor bubbles that rise upwardly through the wicking region in the liquid channel 330. This vapor may be drawn into one or more of the microchannel distillation sections (370, 370a, 370b) through the liquid inlets (376, 376a, 376b) and combined with the vapor phase flowing through the microchannel distillation sections (370, 370a, 370b). Heat exchange fluid flows through heat exchange channels 350 and 360 in a direction that may be co-current or counter-current to the flow of the vapor phase through the process microchannel 310. In one embodiment, the flow of heat exchange fluid through heat exchange channel 350 could be in one direction and the flow of heat exchange fluid through heat exchange channel 360 could be in the opposite direction. The heat exchange fluid heats the process fluids in the process microchannel 310 and the liquid channel 330.

Figure 5:
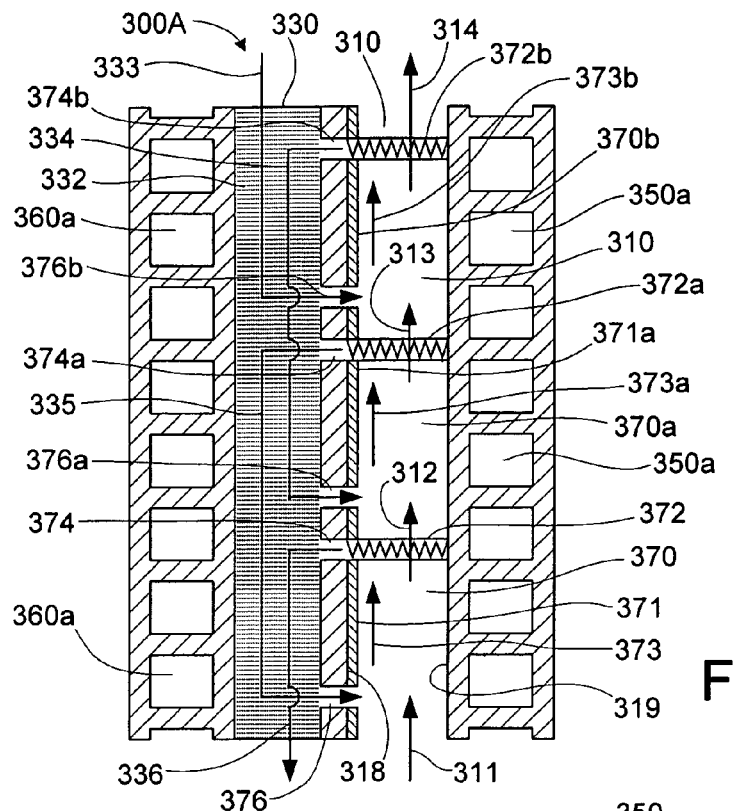
FIG. 5 is a schematic illustration of a microchannel distillation unit that can be used in accordance with the inventive process.

The microchannel distillation unit 300A illustrated in FIG. 5 is identical in design and operation to the microchannel distillation unit 300 illustrated in FIG. 4 with the exception that the microchannel distillation unit 300A provides for the flow of the heat exchange fluid in a cross-current direction relative to the flow of the vapor phase through the process microchannel 310.

Figure 6:
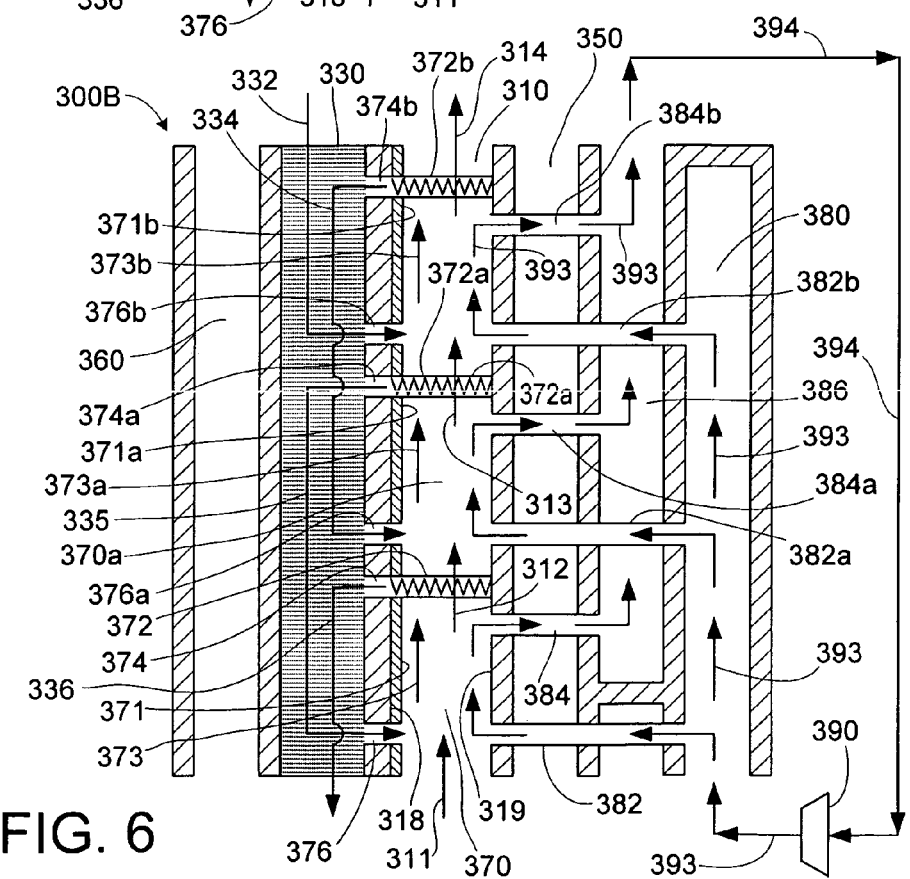
FIG. 6 is a schematic illustration of a microchannel distillation unit that can be used in accordance with the inventive process.

The microchannel distillation unit 300B illustrated in FIG. 6 is identical in design and operation to the microchannel distillation unit 300 illustrated in FIG. 4 with the exception that the microchannel distillation unit 300B employs supplemental vapor channels 380 and 386, and compressor 390. Vapor channel 386 is adjacent to heat exchange channel 350. Vapor channel 380 is adjacent to vapor channel 386. Each of the micro distillation sections (370, 370a, 370b) has a supplemental vapor inlet, for example, a channel or tube (382, 382a, 382b) extending from the vapor phase channel 380 to the process microchannel 310. Each of the microchannel distillation sections (370, 370a, 370b) also has a supplemental vapor outlet, for example, a channel or tube (384, 384a, 384b) extending from the process microchannel 310 to the vapor phase channel 386. The vapor phase channels 380 and 386 may be microchannels, and each may have the same dimensions as the process microchannel 310 or the liquid channel 330. The operation of the microchannel distillation unit 300B is the same as the microchannel distillation unit 300 with the exception that the vapor phase is recirculated through the microchannel distillation unit 300B as a vapor phase rather than being condensed and recirculated through the microchannel distillation unit 300 as a liquid phase. The vapor phase flows from compressor 390, as indicated by arrows 393, through vapor phase channel 380, and from vapor phase channel 380 through each of the vapor phase inlet channels or tubes (382, 382a, 382b) into each of the microchannel distillation sections (370, 370a, 370b) where it combines with vapor phase flowing from reboiler 130, vapor phase flowing from reboiler 130 being indicated by arrows 311, 312, 313 and 314. In the microchannel distillation sections (370, 370a, 370b) the vapor phase contacts the liquid phase flowing along the interior walls (371, 371a, 371b). The liquid phase and the vapor phase undergo a mass transfer in each of the distillation sections (370, 370a, 370b) as described above. Part of the vapor phase flows through the capture structure (372, 372a, 372b) and part of the vapor phase exits the microchannel distillation sections (370, 370a, 370b) through the vapor phase outlet channels (384, 384a, 384b) and flows into vapor phase channel 386. The vapor phase flows from vapor phase channel 386 back to compressor 390 as indicated by line 394.

Figure 7:
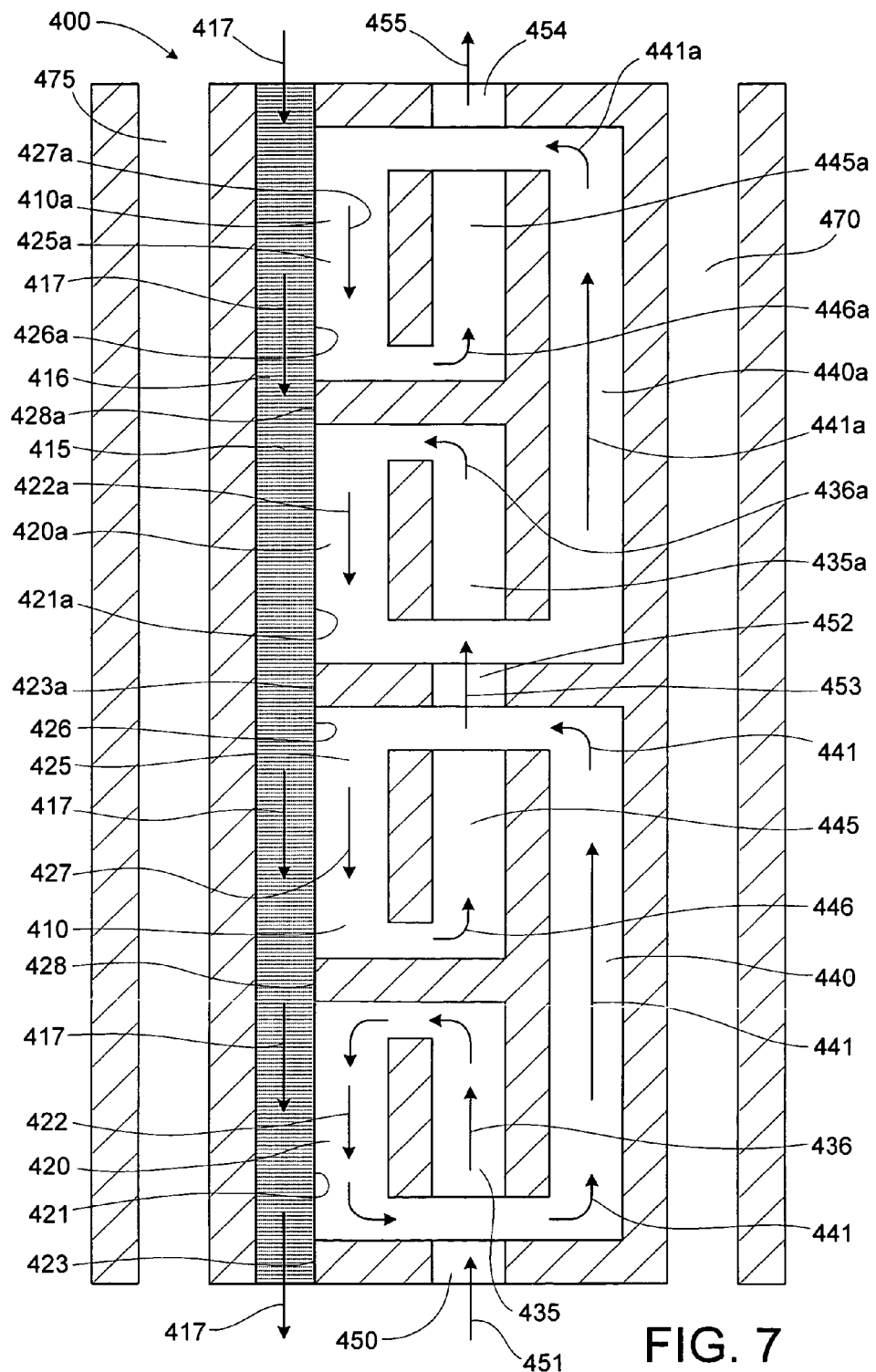
FIG. 7 is a schematic illustration of a microchannel distillation unit that can be used in accordance with the inventive process.

In one embodiment, a microchannel distillation unit that may be used in any of the above-described distillation columns, including distillation columns 100 and 100A, may have the construction illustrated in FIG. 7. Referring to FIG. 7, microchannel distillation unit 400 comprises: liquid channel 415; process microchannels 420, 425, 420a and 425a; vapor channels 435, 440, 445, 435a, 440a and 445a; vapor inlet/outlets 450, 452 and 454; and heat exchange channels 470 and 475. Liquid channel 415 contains wicking region 416. The microchannel distillation unit 400 illustrated in FIG. 10 comprises two microchannel distillation sections, namely, microchannel distillation sections 410 and 410a. It will be understood, however, that although the illustrated embodiment depicts two microchannel distillation sections, the microchannel distillation unit 400 may comprise any desired number of microchannel distillation sections, for example, three, four, five, six, seven, eight, ten, tens, hundreds, thousands, etc. Each of the microchannel distillation sections (410, 410a) comprises a first process microchannel (420, 420a), a second process microchannel (425, 425a), a first vapor channel (435, 435a), a second vapor channel (440, 440a), and a third vapor channel (445, 445a). Microchannel distillation section 410 includes vapor inlet/outlets 450 and 452. The vapor outlet 452 also functions as a vapor inlet for microchannel distillation section 410a. Microchannel distillation section 410a includes vapor inlet/outlets 452 and 454. The process microchannels (420, 425, 420a, 425a) are adjacent to liquid channel 415. Part of the wicking region 416 functions as a wall (421, 426, 421a, 426a) for the process microchannels (420, 425, 420a, 425a). While not wishing to be bound by theory, it is believed that capillary forces in the wicking region (416) maintain a separation between the liquid phase in the wicking region (416) and the vapor phase in the adjacent process microchannels (420, 425, 420a, 425a), while still allowing for mass transfer to occur at the interface between the wicking region and the process microchannels. The lower interior first vapor channels (435, 435a) are adjacent to the lower process microchannels (420, 420a). The upper interior third vapor channels (445, 445a) are adjacent to the upper process microchannels (425, 425a). The outer second vapor channels (440, 440a) are adjacent to the inner first and third vapor channels (435, 445, 435a, 445a). Heat exchange channel 470 is adjacent to the outer vapor channels 440 and 440a, and heat exchange channel 475 is adjacent to liquid channel 415. It will be understood that if the microchannel distillation unit 400 is repeated in a microchannel distillation column, each repetition of the microchannel distillation unit 400 will share a heat exchange channel with the next adjacent microchannel distillation unit 400, thus each repetition of the microchannel distillation unit 400 will have one heat exchange channel. For example, the heat exchange channel 470 of one microchannel distillation unit 400 will also function as the heat exchange channel 475 of the next adjacent microchannel distillation unit 400. The first and third vapor channels (435, 445, 435a, 445a) and the second vapor channels (440, 440a) may be positioned in different planes as illustrated in FIG. 7, or they may be positioned side by side in the same plane. In regions where the second vapor channel (440, 440a) and the first vapor channel (435, 435a) or third vapor channel (445, 445a) appear to cross over one another in FIG. 7, the flow of the vapor phase streams may be maintained in separate planes. For example, the streams shown flowing horizontally in FIG. 7 may flow above the plane of the page, while the streams shown flowing vertically in FIG. 7 may flow below the plane of the page. These streams may be sealed from crossing the plane of the page in such a way as to prevent vapor flow from bypassing any of the microchannel distillation sections (410, 410a). Each of the microchannel distillation sections (410, 410a) contains junctions (423, 428, 423a, 428a) wherein the vapor phase contacts a wall which forms a seal with the liquid phase in the wicking region 416. This seal in combination with capillary forces in the wicking region 416 may prevent vapor from intruding into the wicking region 416 or from bypassing any of the microchannel distillation sections (410, 410a).

In operation, a liquid phase containing components X and Y flows downwardly through the wicking region 416 in the liquid channel 415, as indicated by arrows 417. A vapor phase containing components X and Y flows through vapor inlet/out 450, as indicated by arrow 451, into and through first vapor channel 435 as indicated by arrow 436, and into and through process microchannel 420, as indicated by arrow 422. In the process microchannel 420 the vapor phase contacts at least part of the liquid phase in the wicking region 416. Part of the more volatile component Y transfers from the liquid phase to the vapor phase to form a component Y rich vapor phase. Part of the less volatile component X transfers from the vapor phase to the liquid phase to form a component X rich liquid phase. The vapor phase flows from process microchannel 420 to and through second vapor channel 440, as indicated by arrows 441, and from second vapor channel 440 into and through process microchannel 425, as indicated by arrow 427. In the process microchannel 425, the vapor phase contacts at least part of the liquid phase in the wicking region 416. Part of the more volatile component Y transfers from the liquid phase to the vapor phase to form a component Y rich vapor phase. Part of the less volatile component X transfers from the vapor phase to the liquid phase to form a component X rich liquid phase. The vapor phase flows from process microchannel 425 to and through third vapor channel 445, as indicated by arrow 446, and then to and through vapor inlet/outlet 452, as indicated by arrow 453. The vapor phase flows from vapor inlet/outlet 452 into and through first vapor channel 435a, as indicated by arrow 436a, into and through process microchannel 420a, as indicated by arrow 422a. In the process microchannel 420a, the vapor phase contacts at least part of the liquid phase in the adjacent wicking region 416. Part of the more volatile component Y transfers from the liquid phase to the vapor phase to form a component Y rich vapor phase. Part of the less volatile component X transfers from the vapor phase to the liquid phase to form a component X rich liquid phase. The vapor phase flows from the process microchannel 420a to and through the second vapor channel 440a, as indicated by arrow 441a, and then to and through process microchannel 425a, as indicated by arrow 427a. In the process microchannel 425a, the vapor phase contacts at least part of the liquid phase in the wicking region 416. Part of the more volatile component Y transfers from the liquid phase to the vapor phase to form a component Y rich vapor phase. Part of the less volatile component X transfers from the vapor phase to the liquid phase to form a component X rich liquid phase. The vapor phase flows from the process microchannel 425a to and through the third vapor channel 445a, as indicated by arrow 446a, and to and through vapor inlet/outlet 454, as indicated by arrow 455. The flow of the vapor phase through the microchannel distillation sections (410, 410a) may be driven by a static pressure differential. The flow of the liquid phase through the wicking region 416 may be driven by one or more of gravity, shear force from the vapor phase flowing through the process microchannels (420, 425, 420a, 425a), capillary forces in the wicking region 416, and a pressure differential within liquid held in the wicking region 416 by capillary forces (e.g., inducing flow from the wicking region 416 by suction after the liquid phase in the wicking region 416 separates from the vapor phase in the process microchannels (420, 425, 420a, 425a) and is cooled).

The flow of heat exchange fluid through heat exchange channel 470 may be co-current, cross-current or counter-current relative to the flow of vapor through the second vapor channels (440, 440a). The flow of heat exchange fluid through heat exchange channel 475 may be co-current, cross-current or counter-current relative to the flow of liquid through the liquid channel 415. Each of the heat exchange channels 470 and 475 may be used to form a single or multiple temperature zones along the length of the heat exchange channels 470 and 475. For example, a separate heat exchange zone may be employed for each of the microchannel distillation sections (410, 410a). That is, each of the microchannel distillation sections (410, 410a) may be operated at a different temperature.

Figure 8:
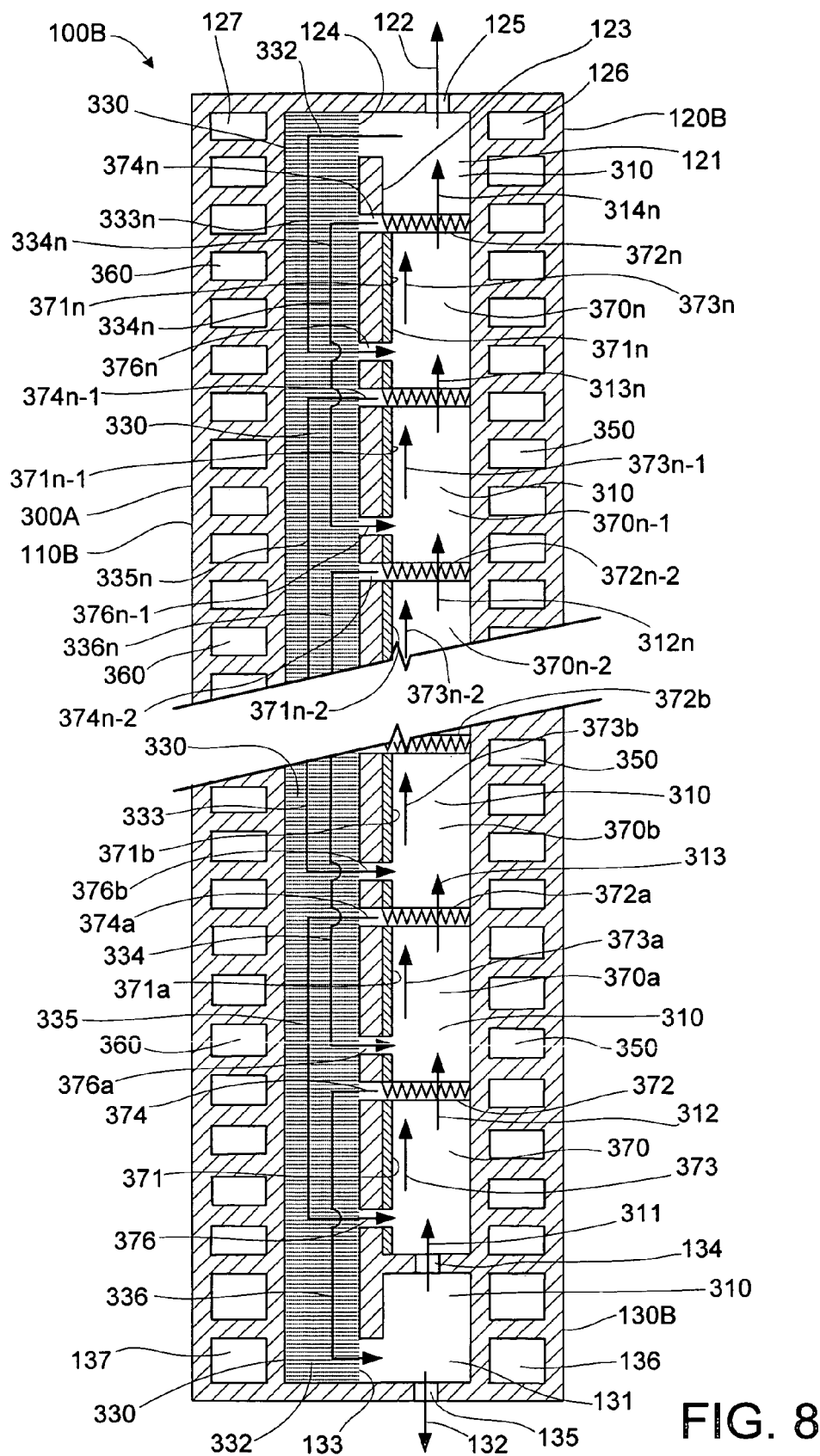
FIG. 8 is a schematic illustration of a microchannel distillation unit that can be used in accordance with the inventive process.

The distillation process 100B illustrated in FIG. 8 is the same as the distillation process 100 illustrated in FIG. 1 except that more detail is provided in FIG. 8. In FIG. 8 distillation column or apparatus 100B is disclosed and the microchannel distillation unit 300A illustrated in FIG. 5 is specifically shown as being used in distillation column or apparatus 110B. Distillation column or apparatus 110B includes microchannel condenser 120B and microchannel reboiler 130B. The microchannel distillation unit 300A illustrated in FIG. 8 contains n microchannel distillation sections 370, that is, microchannel distillation sections 370, 370a, 370b. . . 370n-2, 370-n-1 and 370n, wherein n is a number that can be of any value, for example, 5, 10, 20, 50, 100, 500, 1000, 10000, etc. The broken space in FIG. 8 indicates that distillation sections 370 beyond those illustrated may be provided. The microchannel distillation unit 300A employed in distillation column or apparatus 110B has the same construction and functions in the same manner as the microchannel distillation unit 300A illustrated in FIG. 5. A feed comprising a fluid mixture comprising components X and Y enters distillation column or apparatus 110B. Within the distillation column or apparatus 110B a vapor phase flows through a series of microchannel distillation sections 370 in a direction towards the microchannel condenser 120B and a liquid phase flows through a series of microchannel distillation sections 370 in a direction towards the microchannel reboiler 130B. In each microchannel distillation section 370 the vapor phase and the liquid phase contact each other with the result being a mass transfer between the phases. In each microchannel distillation section 370 part of the more volatile component Y transfers from the liquid phase to the vapor phase, and part of the less volatile component X transfers from the vapor phase to the liquid phase. The vapor phase, which is progressively enriched with the more volatile component Y, flows through microchannel distillation sections 370 towards the microchannel condenser 120B and into the microchannel condenser 120B. The liquid phase, which is progressively enriched with the less volatile component X, flows through the microchannel distillation sections 370 towards the microchannel reboiler 130B and into the microchannel reboiler 130B. The microchannel condenser 120B illustrated in FIG. 8 comprises portions of process microchannel 310 and liquid channel 330, the latter including a portion of wicking region 332. The microchannel condenser 120B also comprises microchannel condenser space 121, interior wall 123, distillate outlets 124 and 125, and heat exchange channels 126 and 127. The microchannel condenser space 121 may have the same dimensions of height and width as the process microchannel 310. The heat exchange channels 126 and 127 may have the same dimensions as the heat exchange channels 350 and 360. In operation, the vapor phase from microchannel distillation section 370n flows through capture structure 372n, as indicated by arrow 314n, into microchannel condenser space 121 wherein the vapor phase is condensed. Part or all of the condensed vapor phase, which may be referred to as distillate product D, flows from microchannel condenser 120B through distillate outlet 125, as indicated by arrow 122. Part or all of the distillate product D may flow through distillate outlet 124 into wicking region 332, and through wicking region 332 to liquid entrance 376n, as indicated by arrow 333n. From that point, the liquid phase flows through the liquid channel 330 and the series of microchannel sections 370n to 370 towards the microchannel reboiler 130B.

The microchannel reboiler 130B illustrated in FIG. 8 comprises portions of process microchannel 310 and liquid channel 330, the latter including a portion of wicking region 332. The microchannel reboiler 130B also includes microchannel reboiler space 131, liquid inlet 133, vapor outlet 134, liquid outlet 135, and heat exchange channels 136 and 137. The microchannel reboiler space 131 may have the same dimensions of height and width as the process microchannel 310. The reboiler heat exchange channels 136 and 137 may have the same dimensions as the heat exchange channels 350 and 360. In operation, the liquid phase from microchannel distillation section 370 flows through liquid inlet 133, as indicated by arrow 336, into microchannel reboiler space 131 wherein part or all of the liquid phase may be vaporized and the remainder remains in liquid form. The part that remains in liquid form, which may be referred to as bottoms product B, flows out of microchannel reboiler 130B through liquid outlet 135, as indicated by arrow 132. The part of the liquid product that is vaporized flows through vapor outlet 134, as indicated by arrow 311, into microdistillation section 370. From that point, the vapor phase flows through the process microchannel 310 and the series of microchannel sections 370 to 370n towards the microchannel condenser 120B.

Although only one microchannel distillation unit (300, 300A, 300B, 400) is illustrated in FIGS. 4-8, there is practically no upper limit to the number of microchannel distillation units into and out of FIGS. 4-8 and from left to right in the figures that may be used in a distillation column or apparatus for conducting the inventive process. For example, one, two, three, four, five, six, eight, ten, twenty, fifty, one hundred, hundreds, one thousand, thousands, ten thousand, tens of thousands, one hundred thousand, hundreds of thousands, millions, etc., of the microchannel distillation units described above may be used. The process microchannels, and associated liquid channels and heat exchange channels may be aligned side-by-side or stacked one above another. In embodiments where more than one microchannel distillation unit is present, the feed must be distributed among the microchannel distillation units and introduced into each microchannel distillation unit at a location that is intermediate between the microchannel reboiler and condenser. This can be accomplished through the addition of feed channels to carry the distributed feed fluids to each microchannel distillation unit or by partitioning off unused portions of existing microchannel distillation units (such as heat exchange channels) which are not used in the region of the microchannel distillation unit where feed is to be distributed and introduced. Those skilled in the art can determine desirable locations along the length of the microchannel distillation unit at which the feed might be introduced. The feed distribution might be accomplished through the aid of a wick distribution structure if a liquid, or through other means, such as distribution through an array of orifices.

Although FIGS. 4-8 depict essentially vertical flow through the channels, these distillation units may be aligned horizontally to provide for horizontal flow through the channels, or they may be aligned at an inclined angle from the horizontal.

Figure 9:
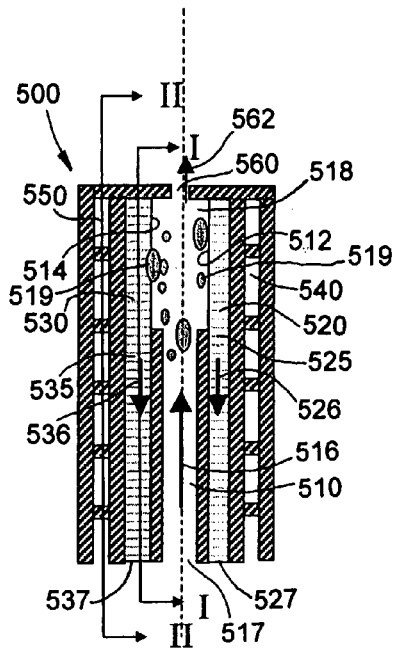
FIG. 9 is a schematic illustration of a microchannel condenser that can be used with the inventive process.
Figure 11:
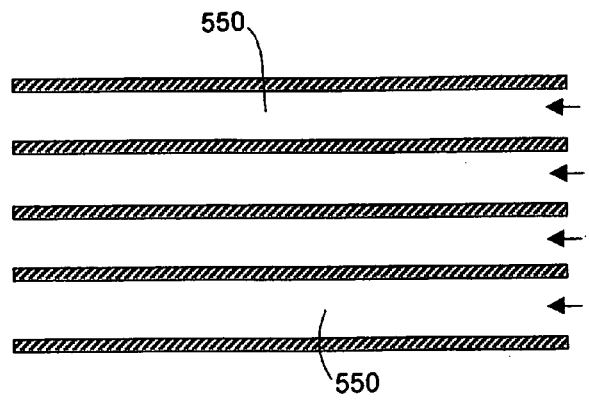
FIG. 11 is a schematic illustration of the microchannel condenser illustrated in FIG. 9 taken along line II-II in FIG. 9.

An alternate embodiment of the microchannel condenser 120 illustrated in FIGS. 1 and 2 and the microchannel condenser 120B illustrated in FIG. 8 is disclosed in FIGS. 9-11. Referring to FIGS. 9-11, microchannel condenser 500 comprises process microchannel 510, liquid channels 520 and 530, heat exchange channels 540 and 550, and outlet 560. Liquid channel 520 includes wicking region 525 and outlet 527, and liquid channel 530 includes wicking region 535 and outlet 537. Process microchannel 510 is positioned between liquid channels 520 and 530. Heat exchange channels 540 are adjacent to liquid channel 520. Heat exchange channels 550 are adjacent to liquid channel 530. Process microchannel 510 includes inlet 511 for permitting vapor to flow into the process microchannel 510, and outlets 512 and 514 for permitting condensed vapor to flow from process microchannel 510 into wicking regions 525 and 535, respectively. In operation, vapor 518 flows through inlet 517 into process microchannel 510 in the direction indicated by arrow 516 and condenses to form condensed vapor 519 which may be referred to as distillation product D. Heat exchange fluid flows through heat exchange channels 540 and 550 in a direction that is crosscurrent relative to the flow of vapor in the process microchannel 510. Part or all of the condensed vapor may flow through outlet 560, as indicated by arrow 562. The remaining condensed vapor may flow through outlets 512 and 514 into wicking regions 525 and 535, respectively. The distillate product flowing in the wicking regions 525 and 535 flows in the direction indicated by arrows 526 and 536 through outlets 527 and 537, respectively.

Figure 12:
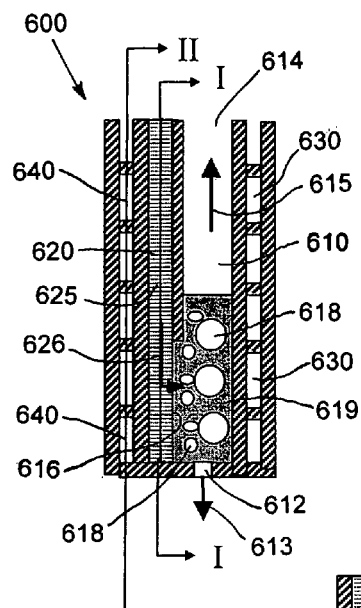
FIG. 12 is a schematic illustration of a microchannel reboiler that can be used with the inventive process.
Figure 13:
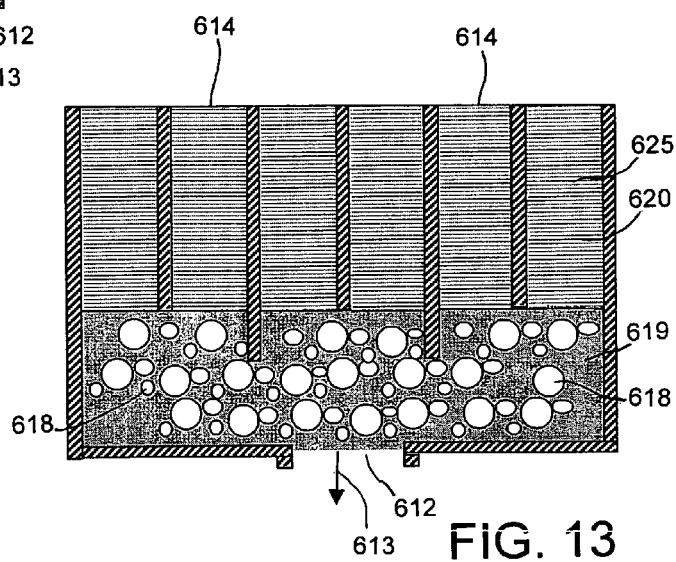
FIG. 13 is a schematic illustration of the microchannel reboiler illustrated in FIG. 12 taken along line I-I in FIG. 12.
Figure 14:
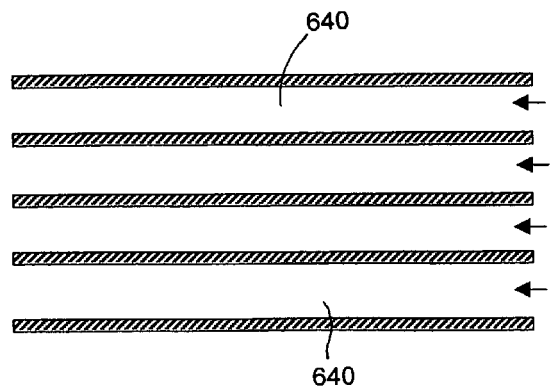
FIG. 14 is a schematic illustration of the microchannel reboiler illustrated in FIG. 12 taken along line II-II in FIG. 12.

An alternate embodiment of the microchannel reboiler 130 illustrated in FIGS. 1 and 2 and the microchannel reboiler 130B illustrated in FIG. 8 is disclosed in FIGS. 12-14. Referring to FIGS. 12-14, microchannel reboiler 600 comprises process microchannel 610, liquid channel 620, and heat exchange channels 630 and 640. Liquid channel 620 includes wicking region 625. Process microchannel 610 is positioned between liquid channel 620 and heat exchange channels 630. Heat exchange channels 640 are adjacent to liquid channel 620. Process microchannel 610 includes outlets 612 and 614, and inlet 616. In operation, liquid 619 flows through wicking region 625 to inlet 616, and through inlet 616 into process microchannel 610, as indicated by arrow 626. Heat exchange fluid flows through heat exchange channels 630 and 640 in a direction that is crosscurrent relative to the flow of liquid through the wicking region 625. Part or all of the liquid 619, which is in the form of bottoms product B, may flow through outlet 612, as indicated by arrow 613. The remainder of the bottoms product B may be vaporized. The vapor 618 flows through process microchannel 610 in the direction indicated by arrow 615 and out of process microchannel 610 through outlet 614.

Figure 15:
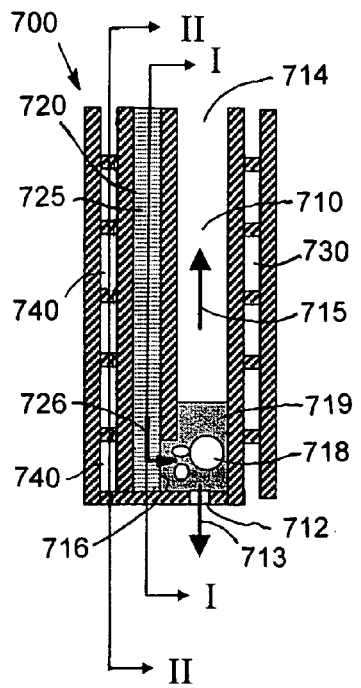
FIG. 15 is a schematic illustration of a microchannel reboiler that can be used with the inventive distillation process.
Figure 16:
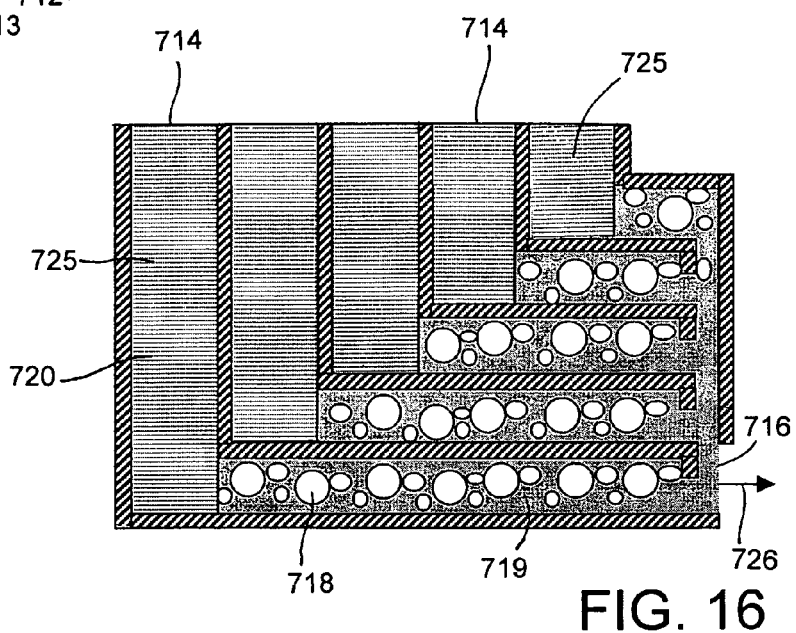
FIG. 16 is a schematic illustration of the microchannel reboiler illustrated in FIG. 15 taken along line I-I in FIG. 15.
Figure 17:
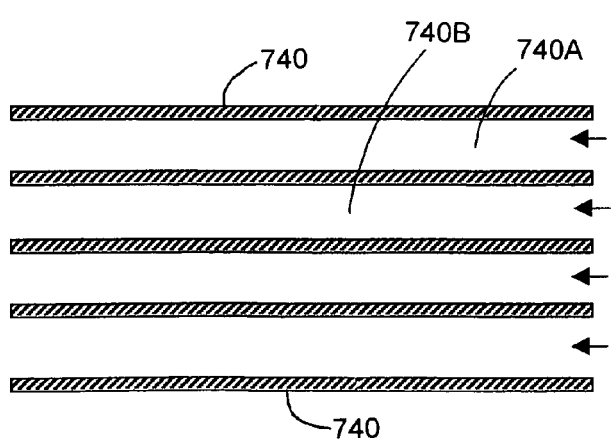
FIG. 17 is a schematic illustration of the microchannel reboiler illustrated in FIG. 15 taken along line II-II in FIG. 15.

An alternate embodiment of the microchannel reboiler 130 illustrated in FIGS. 1 and 2 and the microchannel reboiler 130B illustrated in FIG. 8 is disclosed in FIGS. 15-17. Referring to FIGS. 15-17, microchannel reboiler 700 comprises process microchannel 710, liquid channel 720, and heat exchange channels 730 and 740. Liquid channel 720 includes wicking region 725. Process microchannel 710 is positioned between liquid channel 720 and heat exchange channels 730. Heat exchange channels 740 are adjacent to liquid channel 720. Process microchannel 710 includes outlets 712 and 714, and inlet 716. In operation, liquid 719 flows through wicking region 725 to inlet 716, and through inlet 716 into process microchannel 710, as indicated by arrow 726. Heat exchange fluid flows through heat exchange channels 730 and 740 in a direction that is crosscurrent relative to the flow of liquid through the wicking region 725. Part or all of the liquid 719, which is in the form of bottoms product B, may flow through outlet 712, as indicated by arrow 713. The remainder of the bottoms product B may be vaporized. The vapor 718 flows through process microchannel 710 in the direction indicated by arrow 715 and out of process microchannel 710 through outlet 714.

The microchannel condenser (120, 120B, 500) and microchannel reboiler (130, 130B, 600, 700) as components of the inventive microchannel distillation unit (300, 300A, 300B, 400) can be integrated into the manifolds (header and footer) of the process microchannels (310, 420, 425, 420a, 425a) and liquid channels (330, 415). An example of manifolding with an integrated microchannel reboiler is shown in FIGS. 12-14. The liquid from the last section of the liquid channel (stream 336 in FIG. 8) flows into the footer/reboiler section at the unit end and is heated by the heat exchange channels 630 and 640. Vapor is formed and flows upwards, as indicated by arrow 615, back into the process channels via buoyancy. Part of the liquid is drained through the common outlet 612 at the bottom as the bottoms product so that a splitting of boil-up ratio can be controlled by the flow conditions and configuration of the microchannel reboiler. Another example is illustrated in FIGS. 15-17 where the common outlet of the process channels' footer is located at the side. To prevent carryover of the vapor by the liquid to be drained as product, an extruded edge may be made at the end of each horizontal separation wall. As the heat transfer area is different from channel to channel in a single layer of the unit, the duty of the reboiler microchannel may have to be different. For example, the duty in heat exchange channel 740A may have to be higher than in channel 740B, as horizontal channel 740A is shorter than 740B. Control of the duty in an individual microchannel reboiler heat exchange channel can be made by changing flow rate, inlet temperature and/or pressure.

The manifold (header) may be located at the end of the unit (FIGS. 9-11) where vapor is cooled and partly condensed by the integrated microchannel condenser. The condensation occurs on the wicking structure surface as heat is removed from the wick by the integrated condenser. The condensate may be enriched in the less volatile component and is sucked in by the wicking structure and transported along the liquid channel. The uncondensed vapor leaves the outlet of the manifold so that a reflux is realized. The reflux ratio can be controlled by controlling the duty of the microchannel condenser.

Figure 18:
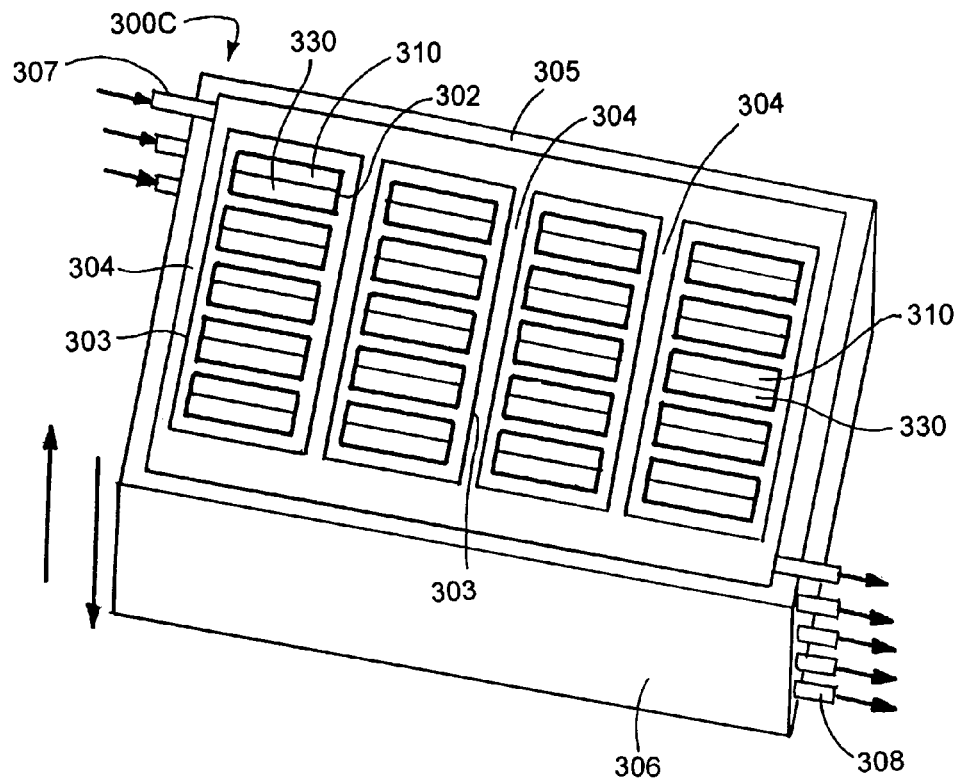
FIG. 18 is a schematic illustration of a microchannel distillation unit that can be used in accordance with the inventive process.

The microchannel distillation unit 300C illustrated in FIG. 18 is a slightly modified version of the microchannel distillation unit 300A illustrated in FIG. 5. The microchannel distillation until 300C contains a plurality of adjacent distillation units 302 arranged in parallel spaced rows 303. Each of the distillation units comprises a process microchannel 310 and an adjacent liquid channel 330. These are the same as discussed above. The rows 303 of distillation units 302 are separated by cross-flow heat exchange channels 304 positioned between the rows 303. Heat exchange manifolds 305 and 306 distribute heat exchange fluid to the heat exchange channels 304. The heat exchange manifold 305 includes heat exchange fluid inlets 307. Heat exchange manifold 306 includes heat exchange fluid outlets 308. This embodiment provides the advantage of avoiding the use of interleaved heat exchange channels while still providing the required temperature profile. In this embodiment each heat exchange channel provides thermal communication with a plurality of process microchannels 310 and liquid channels 330. The microchannel distillation unit 300C employs a separate heat exchange manifold for each layer of heat exchange channels. Alternatively, a common manifold for a plurality of or all of the heat exchange channels can be used.

Each of the process microchannels (310, 420, 425, 420a, 425a, 510, 610, 710) may have a cross section that has any configuration, for example, square, rectangular, circular, oval, trapezoidal, etc. Each of these process microchannels has at least one internal dimension of height or width of up to about 10 mm, and in one embodiment from about 0.05 to about 10 mm, and in one embodiment about 0.001 to about 5 mm, and in one embodiment about 0.05 to about 2 mm, and in one embodiment about 0.05 to about 1.5 mm, and in one embodiment about 0.05 to about 1 mm, and in one embodiment about 0.05 to about 0.5 mm. The other internal dimension of height or width may be of any value, for example, it may range from about 0.01 cm to about 2 cm, and in one embodiment from about 0.01 to about 1 cm, and in one embodiment from about 0.1 to about 1 cm. The length of each of the process microchannels 310 may be of any value, for example, it may range from about 1 to about 200 cm, and in one embodiment about 1 to about 50 cm, and in one embodiment about 2 to about 10 cm. The length of each of the process microchannels 420, 425, 420a, 425a may be in the range from about 0.1 to about 1000 mm, and in one embodiment about 1 to about 100 mm.

The gap between the opposed walls 318 and 319 in each of the microchannel distillation sections (370, 370a, 370b, 370n-2, 370n-1, 370n) may range from about 0.1 to about 20 mm, and in one embodiment from about 1 to about 10 mm. The width of each microchannel distillation section may range from about 1 to about 100 mm, and in one embodiment about 2 to about 50 mm, and in one embodiment about 5 to about 10 mm. The height of each microchannel distillation section (370, 370a, 370b, 370n-2, 370n-1, 370n) from one capture structure (372, 372a, 372b, 372n-2, 372n-1, 372n) to the next capture structure (for example, from capture structure 372 to capture structure 372a) may range from about 2 to about 100 mm, and in one embodiment about 2 to about 75 mm, and in one embodiment about 2 to about 60 mm, and in one embodiment about 2 to about 40 mm, and in one embodiment about 2 to about 25 mm, and in one embodiment about 2 to about 15 mm, and in one embodiment about 2 to about 10 mm, and in one embodiment from about 5 to about 10 mm.

The height of each of the microchannel distillation sections (410, 410a) for microchannel distillation unit 400 from one vapor inlet/outlet to the next, for example, from inlet/outlet 450 to inlet/outlet 452, may be in the range from about 0.1 to about 1000 mm, and in one embodiment about 1 to about 100 mm.

The interior wall (371, 371a, 371b, 371n-2, 371n-1, 371n) may be formed of a material that is suitable for establishing a wetted wall. These materials enhance the adherence of the liquid phase to it as the liquid flows along the interior wall as a thin film. Examples of useful materials include steel (e.g., carbon steel, and the like); monel; inconel; aluminum; titanium; nickel; platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; or a combination of two or more thereof. The wetted wall material may be in the form of a coating or layer of one of the foregoing materials on the surface of microchannel wall 318, the coating or layer having a thickness of about 0.1 to about 500 microns, and in one embodiment about 0.1 to about 250 microns, and in one embodiment about 0.1 to about 100 microns, and in one embodiment about 0.1 to about 50 microns, and in one embodiment about 0.1 to about 10 microns. In one embodiment, the interior wall may be partially wetted with intermittent or continuous non-wetted portions. The thin film flowing along the interior wall, as indicated by arrows 373, 373a, 373b, 373n-2, 373n-1 and 373n may have a thickness of about 0.1 to about 500 microns, and in one embodiment about 0.1 to about 250 microns, and in one embodiment about 0.1 to about 150 microns, and in one embodiment about 0.1 to about 75 microns, and in one embodiment about 1 to about 50 microns.

The capture structure (372, 372a, 372b, 372n-2, 372n-1, 372n) may comprise any structure that captures liquid and permits vapor to flow through it. The capture structure may assist the movement of liquid contacting the capture structure to and through the liquid exits (374, 374a, 374b, 374n-2, 374n-1, 374n) to the wicking region 332. The capture structure may comprise a wire mesh or cones that project from the liquid exits (374, 374a, 374b, 374n-2, 374n-1, 374n). The capture structure may comprise inverted cones, liquid-nonwetting porous structures having a pore size gradient with pore sizes getting larger toward the wicking region 332, liquid-wetting porous structures having a pore size gradient with pore sizes getting smaller toward the wicking region 332, and/or fibers such as found in demisters or filter media. The capture structure may comprise one or more of sintered metal, metal screen, metal foam, and polymer fibers. Mechanisms for capturing dispersed liquid particles include impingement (due to flow around obstructions), Brownian capture (long residence time in high surface area structure), gravity, centrifugal forces (high curvature in flow), or incorporating fields, such as electrical or sonic fields, to induce aerosol particle motion relative to the flow field.

In one embodiment, the capture structures (372, 372a, 372b, 372n-2, 372n-1, 372n) may comprise perforated foil, for example, a perforated foil in the form of expanded tetrahedrally configured filaments. Examples include Delker expanded screens such as 10 AL 16-125 P and 5 Cu 14-125 P. These screens can have one or two orders of magnitude higher permeability than conventional woven screens. In addition, aluminum, copper, and other metal forms of these screens have relatively high thermal conductivities and also enhance heat transfer.

Another use for the capture structure (372, 372a, 372b, 372n-2, 372n-1, 372n) may be to enhance heat transfer. If the capture structure has a high thermal conductivity, it can act as an extended surface for heat transfer. By being in thermal contact with heat exchange channels 350, the capture structure (372, 372a, 372b, 372n-2, 372n-1, 372n) may promote heat transfer between the heat exchange channel and the liquid and vapor phases in the process microchannel 310.

The liquid channels (330, 415, 520, 530, 620, 720) may comprise microchannels although they may have larger dimensions that would not characterize them as microchannels. Each of these channels may have a cross section that has any configuration, for example, square, rectangular, circular, oval, trapezoidal, etc. Each channel may have an internal dimension of height or width in the range up to about 10 mm, and in one embodiment about 0.05 to about 10 mm, and in one embodiment about 0.05 to about 5 mm, and in one embodiment from about 0.05 to about 2 mm, and in one embodiment from about 0.5 to about 1 mm. The other internal dimension may be in the range from about 1 mm to about 100 mm, and in one embodiment about 5 mm to about 50 mm, and in one embodiment about 10 mm to about 20 mm. The length of the liquid channels may be in the range from about 1 cm to about 200 cm, and in one embodiment about 1 cm to about 50 cm, and in one embodiment about 2 to about 10 cm. The separation between each process microchannel 310 and the next adjacent liquid channel 330 may be in the range from about 0.05 mm to about 5 mm, and in one embodiment about 0.2 mm to about 2 mm.

The wicking region (332, 416, 525, 535, 625, 725) may comprise a wick and/or a wicking surface. The wicking region may preferentially retain a wetting fluid by capillary forces. The wicking region may comprise multiple continuous channels or grooves through which liquids may travel by capillary flow. The channels or grooves may be regularly or irregularly shaped. Liquid may migrate through a dry wick, while liquid in a liquid-containing wick can be transported by gravitational force or by applying a pressure differential, to the wick. The capillary pore size in the wicking material may be selected based on the contact angle of the liquid, the intended pressure gradient within the liquid channel and the surface tension of the liquid.

The wick in the wicking region (332, 516, 525, 535, 625, 725) may be made of different materials depending on the liquid that is intended to be transported through the wicking region. The wicking material may be a uniform material, a mixture of materials, a composite material, or a gradient material. For example, the wicking material may be graded by pore size or wettability to help drain liquid in a desired direction. Examples of wicking materials that may be used include: sintered metals, metal screens, metal foams, polymer fibers including cellulosic fibers, as well as other wetting porous materials. The capillary pore sizes in the wicking materials may be in the range of about 10 nm to about 1 mm, and in one embodiment about 100 nm to about 0.1 mm, where these sizes are the largest pore diameters in the cross-section of the wicking material observed by scanning electron microscopy (SEM).

The wicking region (332, 416, 525, 535, 625, 725) may comprise a wicking surface formed on one or more interior walls of the liquid channels. The wicking surface may comprise one or a plurality of grooves formed in one or more interior walls of the liquid channels. The grooves may be formed in the wall separating the liquid channel and the next adjacent process microchannel and/or heat exchange channel. The grooves may be used to assist with liquid capture and/or enhance heat transfer. The grooves may be straight or have tortuous configurations. The grooves may have serpentine configurations. The grooves may be tapered. The grooves may be hemispherical. The grooves may be formed using any suitable technique including etching, sawing, electrodischarge machining, etc. The grooves may be of any length. The grooves may have a depth of about 1 to about 1000 microns, and in one embodiment about 10 to about 500 microns. The grooves may have a width of about 1 to about 1000 microns, and in one embodiment about 10 to about 100 microns. The number of grooves in the wicking region may be in the range from 1 to about 1000 grooves per centimeter as measured across the widths of the grooves, and in one embodiment from 1 to about 100 grooves per centimeter. In one embodiment, the grooves may have a constant or decreasing width from the top to the bottom of the grooves. In one embodiment, the grooves may form a mouth to larger diameter pores for liquid transport. Liquid may migrate through the grooves as a result of capillary flow. The flow of liquid in the grooves may be parallel (co-current or counter-current) or tangential (cross-current) to the flow of vapor in the adjacent process microchannels. The grooves may be oriented to direct the flow of liquid within the liquid channels and/or direct the flow of liquid between microchannel distillation sections. The grooves may be used to manifold the liquid from one microchannel distillation section to another microchannel distillation section. The microchannel distillation sections may be connected through the grooves in parallel or series, upstream or downstream from one another.

In one embodiment, the wicking region (332, 416, 525, 535, 625, 725) may comprise a wick positioned within the liquid channels and a wicking surface (e.g., grooves) formed in one or more of the interior walls of such liquid channels.

In operation, the wicking region (332, 416, 525, 535, 625, 725) may be filled with liquid. When wet or saturated, the wick transports liquid through porous flow passages to a lower pressure zone, such as a lower pressure created by suction.

Punctured and punctured/expanded foils may be used as the wicking material in the wicking region (332, 416, 525, 535, 625, 725) and/or as the capture structures (372, 372a, 372b, 372n-2, 372n-1, 372n). Useful foils include Ultra Thin MicroGrid Precision-Expanded Foils, available from Delker Corporation. These materials are made in a flattened form and a three-dimensional expanded form. Although similar to conventional wire mesh screens, these materials are made from a single thin sheet by punching an array of holes while pulling the material. In the flattened form the holes are an array of diamonds. In the expanded form, the filaments are in a regular tetrahedral configuration. These materials can be made in thicknesses as small as about 0.0015 inch (1.5 mil) and from a variety of metals, including copper, aluminum and nickel.

Fresnel lenses may be used as the wicking material. Wicks that have microchannels having depths of less than about 100 microns, and in one embodiment about 50 to about 100 microns may be used to promote rapid mass transfer.

The wicking region (332, 416, 525, 535, 625, 725) may be prepared by laser machining grooves into a ceramic tape in the green state. These wicks can be made, for example, with grooves less than 50 microns deep with openings less than 100 microns wide. These grooves typically have a rectangular shape. Ceramic wicks have a high surface energy, are chemically inert, and have high temperature stability. Another material that may be used is an intermetallic formed from two or more metals placed in intimate contact during a bonding process and which combine to form an alloy, compound, or metal solution. Useful intermetallics have properties similar to the ceramic materials. An advantage of engineered structures is fine control of the length-scale for mass transfer in the liquid phase which is desirable for distillation.

In one embodiment, the wicking region (332, 416, 525, 535, 625, 725) may not be permitted to dry out during operation since this could result in vapor escaping through the wicking region. One approach to avoid vapor intrusion into the wicking region (332, 416, 525, 535, 625, 725) may be to add a flow restriction in capillary contact with the wick structure entrance, such as a porous structure with a smaller pore size than the wick structure and limiting the magnitude of the suction pressure such that the non-wetting phase(s) cannot displace the wetting phase from the flow restriction. This type of flow restriction may be referred to as a pore throat. In one embodiment, a pore throat may be provided between the wicking region 332 and the liquid exits (374, 374a, 374b, 374n-2, 374n-1, 374n) and/or liquid entrances (376, 376a, 376b, 376n-2, 376n-1, 376n). In one embodiment, a pore throat may be provided between the process microchannels (420, 425, 420a, 425a) and the liquid channel (415) along the process microchannel walls (421, 426, 421a, 426a).

The heat exchanger may be used for cooling, heating or both cooling and heating. The heat exchanger may comprise one or more heat exchange channels (126, 127, 136, 137, 350, 360, 470, 475, 540, 550, 630, 640, 730, 740), electric heating elements, resistance heaters and/or non-fluid cooling elements. These may be adjacent to the process microchannels (310, 420, 425, 420a, 425a, 510, 610, 710), liquid channels (330, 415, 520, 530, 620, 720) and/or vapor channels (380, 386, 435, 440, 445, 435a, 440a, 445a). In one embodiment, the heat exchanger may not be in contact with or adjacent to the process microchannel, liquid channel and/or vapor channel, but rather can be remote from the process microchannel, liquid channel and/or vapor channel. In one embodiment, the heat exchanger may exchange heat with some but not all of the process microchannels, liquid channels and/or vapor channels. In one embodiment, the heat exchanger may exchange heat with some but not all of the microchannel distillation sections (370, 370a, 370b, 370n-2, 370n-1, 370n, 410, 410a). In one embodiment, a single heat exchange channel can be used to heat or cool two or more, for example, two, three, four, five, six, eight, ten, twenty, etc., process microchannels, liquid channels and/or vapor channels. The electric heating element, resistance heater and/or non-fluid cooling element can be used to form one or more walls of the process microchannels, liquid channels and/or vapor channels. The electric heating element, resistance heater and/or non-fluid cooling element can be built into one or more walls of the process microchannels, liquid channels and/or vapor channels. The electric heating elements and/or resistance heaters can be thin sheets, rods, wires, discs or structures of other shapes embedded in the walls of the process microchannels, liquid channels and/or vapor channels. The electric heating elements and/or resistance heaters can be in the form of foil or wire adhered to the process microchannel walls, liquid channel walls, and/or vapor channel walls. Heating and/or cooling may be effected using Peltier-type thermoelectric cooling and/or heating elements. Multiple heating and/or cooling zones may be employed along the length of the process microchannels, liquid channels and/or vapor channels. Similarly, multiple heat exchange fluids at different temperatures may be employed along the length of the process microchannels, liquid channels and/or vapor channels. The heat exchanger can be use to provide precise temperature control within the process microchannels, liquid channels and/or vapor channels. The heat exchanger can be used to provide a different operating temperature for each microchannel distillation section (370, 370a, 370b, 370n-2, 370n-1, 370n, 410, 410a).

The heat exchange channels (126, 127, 136, 137, 350, 360, 470, 475, 540, 550, 630, 640, 730, 740) may be microchannels although they may have larger dimensions that would not characterize them as microchannels. Each of the heat exchange channels may have an internal dimension of height or width of up to about 10 mm, and in one embodiment about 0.05 to about 10 mm, and in one embodiment about 0.05 to about 5 mm, and in one embodiment from about 0.05 to about 2 mm, and in one embodiment from about 0.5 to about 1 mm. The other internal dimension may be of any value, for example, from about 1 mm to about 50 cm, and in one embodiment about 1 mm to about 10 cm, and in one embodiment about 5 mm to about 5 cm. The length of the heat exchange channels may be of any value, for example, from about 5 mm to about 200 cm, and in one embodiment about 1 cm to about 200 cm, and in one embodiment about 1 cm to about 50 cm, and in one embodiment about 2 cm to about 10 cm. The separation between each process microchannel or liquid channel or vapor channel and the next adjacent heat exchange channel may range from about 0.05 mm to about 5 mm, and in one embodiment about 0.2 mm to about 2 mm.

The process microchannels (310, 420, 425, 420a, 425a, 510, 610, 710), liquid channels (330, 415, 520, 530, 620, 720), vapor channels (380, 386, 435, 440, 445, 435a, 440a, 445a), and heat exchange channels (126, 127, 136, 137, 350, 360, 470, 475, 540, 550, 630, 640, 730, 740) may have rectangular cross sections and be aligned in side-by-side vertically oriented interleaved planes or horizontally oriented interleaved stacked planes. These planes can be tilted at an inclined angle from the horizontal. These configurations may be referred to as parallel plate configurations. An array of these rectangular channels can be easily arranged in a compact unit for scale-up.

The flow rate of the vapor phase flowing through the process microchannels (310, 420, 425, 420a, 425a, 510, 610, 710) and vapor channels (380, 386, 435, 440, 445, 435a, 440a, 445a) may be in the range from about 0.001 to about 5 liters per minute (lpm), and in one embodiment about 0.01 to about 2 lpm, and in one embodiment about 0.01 to about 1 lpm. The velocity of the vapor phase flowing through these channels may be in the range from about 0.01 to about 500 meters per second (m/s), and in one embodiment about 0.01 to about 100 m/s, and in one embodiment about 0.1 to about 50 m/s. The Reynolds Number for the vapor phase flowing through these channels may be in the range from about 100 to about 50,000 and in one embodiment about 100 to about 5,000. The guage pressure within these channels may be in the range from about 0.01 to about 1,000 atmospheres, and in one embodiment about 0.01 to about 100 atmospheres, and in one embodiment from about 30 to about 100 atmospheres, and in one embodiment about 50 to about 100 atmospheres.

The flow rate of the liquid phase flowing as a thin film in each microchannel distillation section (370, 370a, 370b, 370n-2, 370n-1, 370n) may range from about 0.0001 to about 1 lpm, and in one embodiment about 0.001 to about 0.1 lpm. The velocity of the thin film flowing in the distillation sections may range from about 0.001 to about 5 m/s, and in one embodiment about 0.001 to about 2 m/s, and in one embodiment about 0.01 to about 1 m/s. The Reynolds Number for the thin film flowing in the distillation sections may range from about 0.01 to about 5000 and in one embodiment about 0.1 to about 1000, assuming the hydraulic diameter of the film is defined as the average film thickness.

The flow rate of the liquid phase flowing through the wicking region (332, 416, 525, 535, 625, 725) in the liquid channels may be in the range from about 0.0001 to about 1 lpm, and in one embodiment about 0.001 to about 0.1 lpm. The velocity of the liquid phase flowing through the liquid channels may be in the range from about 0.0001 to about 5 m/s, and in one embodiment about 0.001 m/s to about 2 m/s. The Reynolds Number for the liquid phase flowing through the liquid channels may be in the range from about 0.01 to about 5,000 and in one embodiment about 1 to about 2,400. Superfacial velocity may be used to define liquid velocity. The guage pressure within the wicking region in the liquid channels may be in the range of about 0.01 to about 1,000 atmospheres, and in one embodiment about 0.01 to about 200 atmospheres. The pressure differential across the wicking region may range from about 0.0001 to about 0.01 atmospheres, and in one embodiment about 0.0001 to about 0.005 atomospheres.

The heat exchange fluid entering the heat exchange channels (126, 127, 136, 137, 350, 360, 470, 475, 540, 550, 630, 640, 730, 740) may have a temperature of about −190° C. to about 400° C., and in one embodiment about −100° C. to about 200° C. The heat exchange fluid exiting the heat exchange channels may have a temperature in the range of about −100° C. to about 300° C., and in one embodiment about −50° C. to about 250° C. The pressure drop for the heat exchange fluid as it flows through the heat exchange channels may range from about 0.0001 to about 5 atmospheres per meter of length of the heat exchange channel (atm/m), and in one embodiment from about 0.001 to about 1 atm/m. The Reynolds Number for the flow of heat exchange fluid flowing through the heat exchange channels may be in the range from about 100 to about 100,000, and in one embodiment about 200 to about 10,000.

The heat exchange fluid may be any fluid. These include air, steam, liquid water, gaseous nitrogen, liquid nitrogen, other gases including inert gases, carbon monoxide, molten salt, oils such as mineral oil, and heat exchange fluids such as Dowtherm A and Therminol which are available from Dow-Union Carbide. The heat exchange fluid may comprise one or more of the liquids or liquid mixtures being separated.

In one embodiment, the heat exchange channels comprise process channels wherein an endothermic or exothermic process is conducted. These heat exchange process channels may be microchannels. Examples of endothermic processes that may be conducted in the heat exchange channels include steam reforming and dehydrogenation reactions. In one embodiment, the incorporation of a simultaneous endothermic reaction to provide an improved heat sink may enable a typical heat flux of roughly an order of magnitude or more above the convective cooling heat flux. Examples of exothermic processes that may be conducted in the heat exchange channels include water-gas shift reactions, methanol synthesis reactions and ammonia synthesis reactions.

In one embodiment, the heat exchange fluid undergoes a phase change as it flows through the heat exchange channels. This phase change provides additional heat addition or removal from the process microchannels or liquid channels beyond that provided by convective heating or cooling. For a liquid heat exchange fluid being vaporized, the additional heat being transferred would result from the latent heat of vaporization required by the heat exchange fluid. An example of such a phase change would be an oil or water that undergoes boiling. In one embodiment, the heat exchange fluid boils or undergoes partial boiling in the heat exchange channels. In one embodiment, the amount of heat exchange fluid boiling in the heat exchange channels may be in the range from about 1 to about 99% by volume of the total amount of heat exchange fluid in the heat exchange channel, and in one embodiment about 5 to about 50% by volume.

The heat flux for convective heat exchange or convective heating in the microchannel distillation unit may range from about 0.01 to about 125 watts per square centimeter of surface area of the process microchannels ($W/cm^2$) in the microchannel distillation unit, and in one embodiment from about 0.1 to about 50 $W/cm^2$, and in one embodiment from about 1 to about 25 $W/cm^2$, and in one embodiment from about 1 to about 10 $W/cm^2$. The heat flux for phase change heat exchange may range from about 1 to about 250 $W/cm^2$, and in one embodiment, from about 1 to about 100 $W/cm^2$, and in one embodiment from about 1 to about 50 $W/cm^2$, and in one embodiment from about 1 to about 25 $W/cm^2$, and in one embodiment from about 1 to about 10 $W/cm^2$.

In one embodiment, each microchannel distillation section (370, 370a, 370b, 370n-2, 370n-1, 370n, 410, 410a) may be operated at or near isothermal conditions. That is, the temperature within each microchannel distillation section may be maintained at a level that varies by no more than about 5° C., and in one embodiment no more than about 2° C. In one embodiment, the temperature in each microchannel distillation section (370, 370a, 370b, 370n-2, 370n-1, 370n, 410, 410a), microchannel condenser (120, 120B, 500), and/or microchannel reboiler (130, 130B, 600, 700) may be controlled by employing partially boiling heat exchange fluids in the heat exchange channels (126, 127, 136, 137, 350, 360, 470, 475, 540, 550, 630, 640, 730, 740) adjacent to the microchannel distillation sections, microchannel condenser and/or microchannel reboiler. The heat exchange channels may be divided into separate heat exchange channel zones. The heat exchange channel zones within each heat exchange channel may be formed by dividing the heat exchange channel into separate heat exchange channel zones using passive structures (i.e., obstructions), orifices at the inlet and outlet of each heat exchange channel zone, and/or by using mechanisms that control the flow rate and/or pressure of the heat exchange fluid in each of the heat exchange channel zones. Each heat exchange channel may be divided into any number of separate heat exchange channel zones, for example, from 2 to about 2000 heat exchange channel zones, and in one embodiment from 2 to about 200 heat exchange channel zones. Each of the heat exchange channel zones may provide heat exchange with any number of microchannel distillation sections. The number of microchannel distillation sections exchanging heat with each heat exchange channel zone may be in the range from 1 to about 100, and in one embodiment from 1 to about 10. In one embodiment, each microchannel distillation section exchanges heat with a separate heat exchange channel zone. The pressure within each heat exchange channel zone may be controlled using the foregoing passive structures, orifices and/or mechanisms. By controlling the pressure within each heat exchange channel zone, the temperature within each heat exchange channel zone can be controlled. A higher inlet pressure for each heat exchange fluid may be used where the passive structures, orifices and/or mechanisms let down the pressure to the desired heat exchange channel zone pressure. By controlling the temperature within each heat exchange channel zone, the temperature in the adjacent microchannel distillation section or sections can be controlled. Thus, for example, each microchannel distillation section may be operated at a desired temperature by employing a specific pressure in the heat exchange channel zone adjacent to the microchannel distillation section. This provides the advantage of precisely controlled temperatures for each microchannel distillation section. The use of precisely controlled temperatures for each microchannel distillation section provides the advantage of a tailored temperature profile and an overall reduction in the energy requirements for the distillation process. In one embodiment, this process may approach the energy requirements for a reversible distillation process.

The vapor phase and the liquid phase may contact each other in each microchannel distillation section (370, 370a, 370b, 370n-2, 370n-1, 370n, 410, 410a) for a sufficient period of time to achieve at least about 25% by volume of the equilibrium composition for the fluid mixture being treated, and in one embodiment at least about 50% by volume, and in one embodiment at least about 70% by volume. The contact time for the contacting of the vapor and the liquid within each microchannel distillation section may be in the range from about 1 to about 200 milliseconds (ms), and in one embodiment from about 1 to about 10 ms.

The microchannel distillation units (300, 300A, 300B, 300C, 400), microchannel condensers (120, 120B, 500) and microchannel reboilers (130, 130B, 600, 700) may be made of any material that provides sufficient strength, dimensional stability and heat transfer characteristics to permit the operation of the inventive process. These materials include: steel (e.g., stainless steel, carbon steel, and the like); monel; inconel; aluminum; titanium; nickel; platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; silicon carbide; boron carbide; metal carbides such as aluminum carbide; silicon nitride; boron nitride; metal nitrides such as aluminum nitride; or a combination of two or more thereof. The microchannel distillation units may be fabricated using known techniques including wire electrodischarge machining, conventional machining, laser cutting, photochemical machining, electrochemical machining, molding, water jet, stamping, etching (for example, chemical, photochemical or plasma etching) and combinations thereof. The microchannel distillation units may be constructed by forming sheets or layers of material with portions removed that allow flow passage. A stack of sheets may be assembled via diffusion bonding, laser welding, diffusion brazing, and similar methods to form an integrated device. The microchannel distillation units may be assembled using a combination of sheets or laminae and partial sheets or strips. In this method, the channels or void areas may be formed by assembling strips or partial sheets to reduce the amount of material required. The assembly method may include the addition of wicking structures held adjacent to the liquid channel walls. The microchannel distillation units have appropriate manifolds, valves, conduit lines, etc. to control the flow of process fluids and heat exchange fluids. These are not shown in the drawings, but can be provided by those skilled in the art.

The inventive process may be used to separate any two or more fluids that have different volatilities. The process is particularly suitable for handling difficult separations such as ethane from ethylene wherein the fluids being separated have very similar volatilities. Examples of the separations that can be advantageously effected using the inventive process include, in addition to ethane from ethylene, styrene from ethylbenzene separation and associated purification of styrene monomer in an ethylbenzene dehydrogenation plant, separation of oxygen from nitrogen in the cryogenic towers of an air separation plant, separation of cyclohexane from cyclohexanol/cyclohexanone in a nylon monomers plant, deisobutanizers in a gasoline alkylation plant, naphtha splitters upstream from a naphtha reforming plant, and the like.

In one embodiment, the inventive process may be operated at a higher pressure and with more microchannel distillation sections (370, 370a, 370b, 370n-2, 370n-1, 370n, 410, 410a) than conventional processes not employing microchannel distillation sections. With higher pressures and more microchannel distillation sections, the inventive process can be operated using higher temperature heat exchange fluids as compared to conventional processes. This reduces the amount of cryogenic heat exchange fluid required for many separations. For example, for the separation of ethane from ethylene, conventional processes operating at pressures of about 10 to about 25 atmospheres employ heat exchange fluids at temperatures as low as about −150° C., while with the inventive process operating at higher pressures, for example guage pressures in the range of about 30 to about 100 atmospheres, and in one embodiment about 50 to about 100 atmospheres, heat exchange fluids at a temperature of about −30° C. to about 200° C. may be used to effect separation. With the inventive process operating in the above-indicated pressure range and using higher temperature heat exchange fluids, the separation of ethane from ethylene at a purity level of about 99 mole % or higher can be effected using about 10 to about 500 microchannel distillation sections. On the other hand, conventional ethane/ethylene separations at pressures of about 10 to about 25 atmospheres using a heat exchange fluid at temperatures in the range of about −150° C. to about 0° C. typically require about 200 distillation sections. The cost of additional distillation sections using conventional processes to operate at the higher pressures and temperatures indicated above for the inventive process would typically be significantly higher than with the inventive process. On the other hand, the cost of additional microchannel distillation sections with the inventive process are typically relatively low. The use of higher temperature heat exchange fluids with the inventive process should lower the operating cost of the process.

A disadvantage of conventional hardware used for vapor-liquid contacting unit operations is that conventional trays and packing may be difficult to operate or operate less efficiently when the process is operated at feed rates below about 50% design capacity. An advantage of the present invention relates to an ability to operate the process in a modular fashion for effective operation at a wide range of capacities. The inventive process may be designed with numerous modules and sections of modules. Turndown operation can be achieved with directing flows to active modules and sections of modules, where the process channels are operating efficiently at close capacity. For example, an overall process may be operating at 50% capacity, but the active process microchannels may be operating at 80-90% capacity.

In one embodiment, the present invention provides for the separation of ethylene from a fluid mixture comprising ethylene and ethane in a distillation unit having a height of up to about 20 meters, and in one embodiment up to about 10 meters, and in one embodiment up to about 5 meters, and in one embodiment up to about 3 meters, with purity levels of ethylene of at least about 95% by volume, and in one embodiment at least about 98% by volume, and in one embodiment at least about 99% by volume.

In one embodiment, the inventive process exhibits a microchannel fast response to a step change. The test criterion for determining whether a system exhibits a microchannel fast response to a step change may be measured by either of the following Tests 1 or 2.

Test 1

The steady-state distillate and bottoms compositions and flow rates are measured. Then a step change decrease of 10% is made to the total inlet flow rate fed to the distillation column (time=0 minutes). After twenty minutes (t=20 minutes), the distillate and bottoms compositions and flow rates are measured. After 6 hours (time=380 minutes), the distillate and bottoms compositions and flow rates are measured again. Changes in flow rate and mole fraction of key light (the component which just prior to time=0 minutes has the largest mole fraction in the distillate) are compared for the time interval 0 to 20 minutes and 0 to 380 minutes in the bottoms and in the distillate. If the change in flow rate or mole fraction of light key for the time interval 0 to 20 minutes is greater than 80% of the change in flow rate or mole fraction of light key for the time interval 0 to 380 minutes for either the bottoms or distillate product streams, then the device exhibits microchannel fast response to a step change.

Test 2

The steady-state distillate and bottoms compositions and flow rates are measured. Then a step change increase of 10% is made to the mole fraction of light key (the component which just prior to time=0 minutes has the largest mole fraction in the distillate) in the stream fed to the distillation column (time=0 minutes). After twenty minutes (time=20 minutes), the distillate and bottoms compositions and flow rates are measured. After 6 hours (time=380 minutes), the distillate and bottoms compositions and flow rates are measured again. Changes in flow rate and mole fraction of key light (the component which just prior to time=0 minutes has the largest mole fraction in the distillate) are compared for the time interval 0 to 20 minutes and 0 to 380 minutes in the bottoms and in the distillate. If the change in flow rate or mole fraction of light key for the time interval 0 to 20 minutes is greater than 80% of the change in flow rate or mole fraction of light key for the time interval 0 to 380 minutes for either the bottoms or distillate product streams, then the device exhibits microchannel fast response to a step change.

Figure 19:
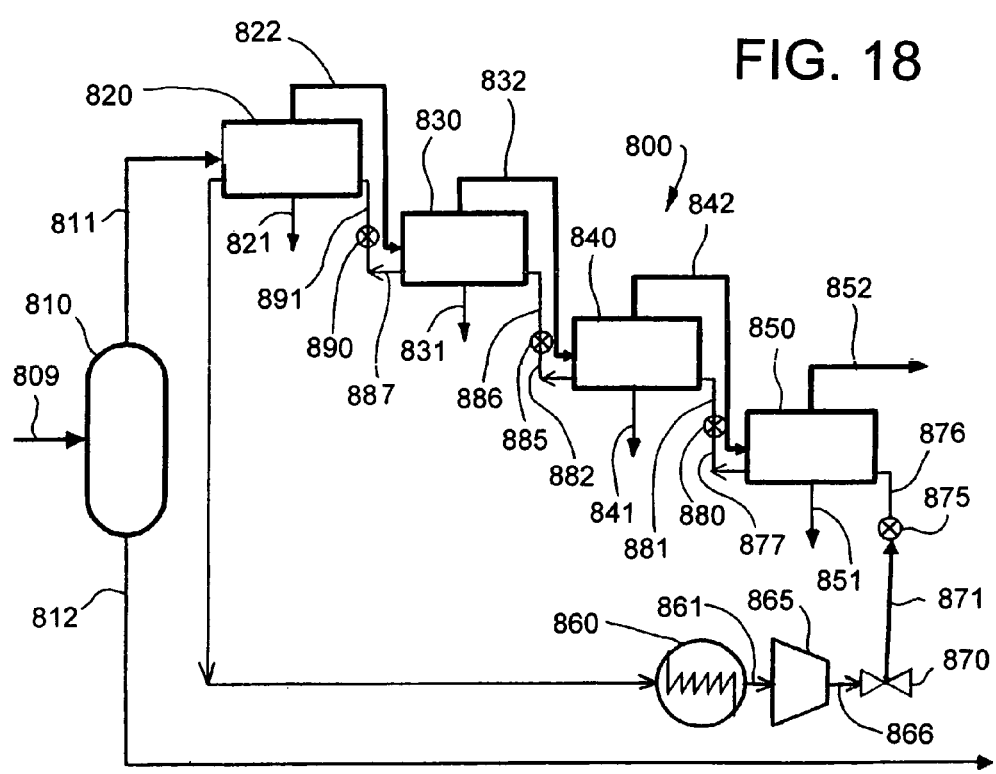
FIG. 19 is a schematic illustration showing a process using the inventive microchannel distillation units for separating water, butanes or butylenes, propanes or propylenes, and ethane or ethylene, from raw natural gas.

The inventive process may be employed in a process for making liquefied natural gas. This is illustrated in FIG. 19. The separation system illustrated in FIG. 19 involves the use of a series of cascaded microchannel distillation units for separating water and higher molecular weight materials such as ethane or ethylene, propanes or propylene, and butanes or butylene, from the raw natural gas. Referring to FIG. 19, separation system 800 includes the use of bulk liquids separator 810, microchannel distillation units 820, 830, 840 and 850, condenser 860, compressor 865, valve 870, and expansion devices 875, 880, 885 and 890. Each of the microchannel distillation units 820, 830, 840 and 850 may be similar in design and operation to the distillation column or apparatus 110B illustrated in FIG. 8 and discussed above. A raw natural gas product mixture comprising methane, water and hydrocarbons containing two or more carbon atoms, enters bulk liquids separator 810 through line 809. Hydrocarbons of about 5 carbon atoms and above are separated from the raw natural gas product mixture and advanced to storage or further processing through line 812. The remainder of the raw natural gas product mixture containing water and hydrocarbons of 1 to about 4 carbon atoms is advanced through line 811 to microchannel distillation unit 820. Water is separated from the product mixture in microchannel distillation unit 820 and is removed from microchannel distillation unit 820 through line 821. The remainder of the raw natural gas product mixture flows through line 822 to microchannel distillation unit 830. Butanes and butylenes are separated from the natural gas product mixture in microchannel distillation unit 830 and flow from microchannel distillation unit 830 through line 831. The remainder of the raw natural gas product mixture flows through line 832 to microchannel distillation unit 840 where propanes and propylene are separated from the product mixture. Propanes and propylene flow from the microchannel distillation unit 840 through line 841. The remainder of the product mixture flows through line 842 to microchannel distillation unit 850. In microchannel distillation unit 850 ethane and ethylene are separated from the product mixture and flow from microchannel distillation unit 850 through line 851. The remaining product comprises methane which flows from microchannel distillation unit 850 through line 852. The raw natural gas product mixture flowing through line 809 to bulk liquids separator 810 may be at a pressure of about 10 to about 5000 psig, and in one embodiment about 10 to about 2500 psig; and a temperature of about −250 to about 500° C., and in one embodiment about −50 to about 300° C. The product mixture flowing through line 811 to microchannel distillation unit 820 may be at a pressure of about 10 to about 5000 psig, and in one embodiment about 10 to about 2500 psig; and a temperature of about −250 to about 500° C., and in one embodiment about −50 to about 300° C. The product mixture flowing through line 822 to microchannel distillation unit 830 may be at a pressure of about 10 to about 5000 psig, and in one embodiment about 10 to about 2500 psig; and a temperature of about −250 to about 500° C., and in one embodiment about −200 to about 300° C. The product mixture flowing through line 832 to microchannel distillation unit 840 may be at a pressure of about 10 to about 5000 psig, and in one embodiment about 10 to about 2500 psig; and a temperature of about −225 to about 500° C., and in one embodiment about −200 to about 300° C. The product mixture flowing through line 842 to microchannel distillation unit 850 may be at a pressure of about 10 to about 5000 psig, and in one embodiment about 10 to about 2500 psig; and a temperature of about −245 to about 500° C., and in one embodiment about −200 to about 300° C. The methane flowing from microchannel distillation unit 850 through line 852 may be at a pressure of about 10 to about 5000 psig, and in one embodiment about 10 to about 2500 psig; and a temperature of about −245 to about 300° C., and in one embodiment about −200 to about 300° C.

The refrigerant used in the separation system 800 illustrated in FIG. 19 may be any refrigerant. The refrigerant flows through line 859 to condenser 860, through condenser 860 to line 861, through line 861 to compressor 865, through compressor 865 to line 866, through line 866 to valve 870, through valve 870 to line 871, through line 871 to expansion device 875, through expansion device 875 to line 876, through line 876 to microchannel distillation unit 850, through heat exchanger 850 to line 877, through line 877 to expansion device 880, through expansion device 880 to line 881, through line 881 to microchannel distillation unit 840, through microchannel distillation unit 840 to line 882, through line 882 to expansion device 885, through expansion device 885 to line 886, through line 886 to microchannel distillation unit 830, through microchannel distillation unit 830 to line 887, through line 887 to expansion device 890, through expansion device 890 to line 891, through line 891 to microchannel distillation unit 820, through microchannel distillation unit 820 to line 859, and through line 859 back to condenser 860 where the cycle starts all over again. The refrigerant flowing through line 859 from microchannel distillation unit 820 to condenser 860 may be at a pressure of about 10 to about 3000 psig, and in one embodiment about 20 to about 2500 psig; and a temperature of about −250 to about 300° C., and in one embodiment about −225 to about 300° C. The refrigerant flowing through line 861 from condenser 860 to compressor 865 may be at a pressure of about 10 to about 3000 psig, and in one embodiment about 20 to about 2500 psig; and a temperature of about −250 to about 300° C., and in one embodiment about −225 to about 300° C. The refrigerant flowing through line 866 from compressor 865 to valve 870 may be at a pressure of about 10 to about 3000 psig, and in one embodiment about 20 to about 2500 psig; and a temperature of about −250 to about 300° C., and in one embodiment about −225 to about 300° C. The refrigerant flowing through line 871 from valve 870 to expansion device 875 may be at a pressure of about 10 to about 3000 psig, and in one embodiment about 20 to about 2500 psig; and a temperature of about −250 to about 300° C., and in one embodiment about −225 to about 300° C. The refrigerant flowing through line 876 from expansion device 875 to microchannel distillation unit 850 may be at a pressure of about 10 to about 3000 psig, and in one embodiment about 20 to about 2500 psig; and a temperature of about −250 to about 300° C., and in one embodiment about −225 to about 300° C. The refrigerant flowing through line 877 from microchannel distillation unit 850 to expansion device 880 may be at a pressure of about 10 to about 3000 psig, and in one embodiment about 20 to about 2500 psig; and a temperature of about −250 to about 300° C., and in one embodiment about −225 to about 300° C. The refrigerant flowing through line 881 from expansion device 880 to microchannel distillation unit 840 may be at a pressure of about 10 to about 3000 psig, and in one embodiment about 20 to about 2500 psig; and a temperature of about −250 to about 300° C., and in one embodiment about −225 to about 300° C. The refrigerant flowing through line 882 from microchannel distillation unit 840 to expansion device 885, may be at a pressure of about 10 to about 3000 psig, and in one embodiment about 20 to about 2500 psig; and a temperature of about −250 to about 300° C., and in one embodiment about −225 to about 300° C. The refrigerant flowing through line 886 from expansion device 885 to microchannel distillation unit 830 may be at a pressure of about 10 to about 3000 psig, and in one embodiment about 20 to about 2500 psig; and a temperature of about −250 to about 300° C., and in one embodiment about −225 to about 300° C. The refrigerant flowing through line 887 from microchannel distillation unit 830 to expansion device 890 may be at a pressure of about 10 to about 3000 psig, and in one embodiment about 20 to about 2500 psig; and a temperature of about −250 to about 300° C., and in one embodiment about −225 to about 300° C. The refrigerant flowing through line 891 from expansion device 890 to microchannel distillation unit 820 may be at a pressure of about 10 to about 3000 psig, and in one embodiment about 20 to about 2500 psig; and a temperature of about −250 to about 300° C., and in one embodiment about −225 to about 300° C.

While the invention has been explained in reaction to specific embodiments, it is to be understood that various modifications thereof will become apparent to those skilled in the art upon reading the specification. Therefore, it is to be understood that the invention disclosed herein is intended to cover such modifications as fall within the scope of the appended claims.

The invention claimed is:

1. A process for distilling a fluid mixture in a microchannel distillation unit, the microchannel distillation unit comprising a plurality of microchannel distillation sections, each microchannel distillation section comprising a liquid inlet and a liquid outlet and a vapor inlet and a vapor outlet, the fluid mixture comprising a more volatile component and a less volatile component, the process comprising:

flowing a vapor phase of the fluid mixture in the first microchannel distillation section in contact with a liquid phase of the fluid mixture, part of the more volatile component transferring from the liquid phase to the vapor phase to form a more volatile component rich vapor phase, part of the less volatile component transferring from the vapor phase to the liquid phase to form a less volatile component rich liquid phase;

separating the more volatile component rich vapor phase from the less volatile component rich liquid phase;

flowing the less volatile component rich liquid phase to the another microchannel distillation section upstream from the first microchannel distillation section; and flowing the more volatile rich vapor phase to the another microchannel distillation section downstream from the first microchannel distillation section.

2. The process of claim 1 wherein each microchannel distillation section comprises at least one process microchannel and at least one adjacent liquid channel, the liquid channel comprising a wicking region.

3. The process of claim 1 wherein the microchannel distillation unit further comprises a heat exchanger.

4. A process for distilling a fluid mixture in a microchannel distillation unit, the microchannel distillation unit comprising a plurality of microchannel distillation sections, the fluid mixture comprising a more volatile component and a less volatile component, the process comprising:

flowing a vapor phase of the fluid mixture in a first microchannel distillation section in contact with a liquid phase of the fluid mixture, part of the more volatile component transferring from the liquid phase to the vapor phase to form a more volatile component rich vapor phase, part of the less volatile component transferring from the vapor phase to the liquid phase to form a less volatile component rich liquid phase;

separating the more volatile component rich vapor phase from the less volatile component rich liquid phase;

flowing the less volatile component rich liquid phase to another microchannel distillation section upstream from the first microchannel distillation section; and flowing the more volatile rich vapor phase to another microchannel distillation section downstream from the first microchannel distillation section;

wherein each microchannel distillation section comprises at least one process microchannel and at least one adjacent liquid channel, the liquid channel comprising a wicking region; and wherein for each microchannel distillation section the process microchannel comprises a liquid inlet for permitting liquid to flow into the process microchannel, a liquid outlet for permitting liquid to flow out of the process microchannel, an interior wall extending from the liquid inlet to the liquid outlet; and a capture structure, the liquid outlet being downstream from the liquid inlet.

5. The process of claim 4 wherein the liquid phase flows along the surface of the interior wall, the liquid phase being in the form of a thin film.

6. The process of claim 2 wherein part of the wicking region forms a wall of the process microchannel.

7. The process of claim 6 wherein the liquid phase flows in the wicking region and the vapor phase flows in the process microchannel and contacts at least part of the liquid phase in the wicking region.

8. The process of claim 1 wherein the more volatile component rich vapor phase is a first section more volatile component rich vapor phase formed in the first microchannel distillation section of the process microchannel, the process microchannel comprising the first microchannel distillation section and downstream second and third microchannel distillation sections, the first section more volatile component rich vapor phase flowing from the first microchannel distillation section into the downstream second microchannel distillation section, a downstream third section less volatile component rich liquid phase formed in the downstream third microchannel distillation section flowing from the downstream third microchannel distillation section into the downstream second microchannel distillation section and contacting the first section more volatile component rich vapor phase in the downstream second microchannel distillation section, the downstream third section less volatile component rich liquid phase flowing in a thin film along an interior wall in the downstream second microchannel distillation section, part of the more volatile component transferring from the downstream third section less volatile component rich liquid phase to the first section more volatile component rich vapor phase to form a downstream second section more volatile component rich vapor phase, part of the less volatile component transferring from the first section more volatile component rich vapor phase to the downstream third section less volatile component rich liquid phase to form a downstream second section less volatile component rich liquid phase; and separating the downstream second section more volatile component rich vapor phase from the downstream second section less volatile component rich liquid phase.

9. The process of claim 1 wherein the less volatile component rich liquid phase is a first section less volatile component rich liquid phase formed in the first microchannel distillation section of the process microchannel, the process microchannel comprising the first microchannel distillation section and upstream second and third microchannel distillation sections, the first section less volatile component rich liquid phase flowing from the first microchannel distillation section into the upstream second microchannel distillation section, an upstream third section more volatile component rich vapor phase formed in the upstream third microchannel distillation section flowing from the upstream third microchannel distillation section into the upstream second microchannel distillation section and contacting the first section less volatile component rich liquid phase in the upstream second microchannel distillation section, the first section less volatile component rich liquid phase flowing in a thin film along an interior wall in the upstream second microchannel distillation section, part of the more volatile component transferring from first section less volatile component rich liquid phase to the upstream third section more volatile component rich vapor phase to form an upstream second section more volatile component rich vapor phase, part of the less volatile component transferring from the upstream third section more volatile component rich vapor phase to the first section less volatile component rich liquid phase to form an upstream second section less volatile component rich liquid phase; and separating the upstream second section more volatile component rich vapor phase from the upstream second section less volatile component rich liquid phase.

10. The process of claim 2 wherein each microchannel distillation section further comprises a heat exchange channel adjacent to the liquid channel, the process microchannel, or both the liquid channel and the process microchannel.

11. A process for distilling a fluid mixture in a microchannel distillation unit, the microchannel distillation unit comprising a plurality of microchannel distillation sections, the fluid mixture comprising a more volatile component and a less volatile component, the process comprising:

flowing a vapor phase of the fluid mixture in a first microchannel distillation section in contact with a liquid phase of the fluid mixture, part of the more volatile component transferring from the liquid phase to the vapor phase to form a more volatile component rich vapor phase, part of the less volatile component transferring from the vapor phase to the liquid phase to form a less volatile component rich liquid phase;

separating the more volatile component rich vapor phase from the less volatile component rich liquid phase;

flowing the less volatile component rich liquid phase to another microchannel distillation section upstream from the first microchannel distillation section; and flowing the more volatile rich vapor phase to another microchannel distillation section downstream from the first microchannel distillation section;

wherein each microchannel distillation section comprises a liquid channel, a first process microchannel, a second process microchannel, a first vapor channel, a second vapor channel, a third vapor channel, a vapor inlet and a vapor outlet, the first process microchannel and the second process microchannel being adjacent to the liquid channel, the liquid channel comprising a wicking region, part of the wicking region forming a wall of the first process microchannel and a wall of the second process microchannel, the liquid phase flowing through the wicking region, the vapor phase flowing through the vapor inlet into the first vapor channel, through the first vapor channel into the first process microchannel, through the first process microchannel in contact with at least part of the liquid phase in the wicking region, from the first process microchannel into the second vapor channel, through the second vapor channel into the second process microchannel, through the second process microchannel in contact with at least part of the liquid phase in the wicking region, from the second process microchannel into the third vapor channel, and through the third vapor channel into the vapor outlet.

12. The process of claim 2 wherein the process microchannel has an internal dimension of width or height of up to about 10 mm.

13. The process of claim 2 wherein the process microchannel has an internal dimension of width or height of up to about 2 mm.

14. The process of claim 2 wherein the process microchannel is made of a material comprising: steel; monel; inconel; aluminum; titanium; nickel; copper; brass; an alloy of any of the foregoing metals; a polymer; ceramics; glass; a composite comprising a polymer and fiberglass; quartz; silicon; or a combination of two or more thereof.

15. The process of claim 2 wherein the liquid channel comprises a microchannel.

16. The process of claim 2 wherein the liquid channel has an internal dimension of width or height of up to about 10 mm.

17. The process of claim 2 wherein the liquid channel has an internal dimension of width or height of up to about 2 mm.

18. The process of claim 2 wherein the liquid channel is made of a material comprising: steel; monel; inconel; aluminum; titanium; nickel; copper; brass; an alloy of any of the foregoing metals; a polymer; ceramics; glass; a composite comprising polymer and fiberglass; quartz; silicon; silicon carbide; boron carbide; metal carbide; silicon nitride; boron nitride; metal nitride; or a combination of two or more thereof.

19. The process of claim 3 wherein the heat exchanger comprises at least one heat exchange channel having an internal dimension of width or height of up to about 10 mm.

20. The process of claim 3 wherein the heat exchanger comprises at least one heat exchange channel having an internal dimension of width or height of up to about 2 mm.

21. The process of claim 3 wherein the heat exchanger comprises at least one heat exchange channel made of a material comprising: steel; monel; inconel; aluminum; titanium; nickel; copper; brass; an alloy of any of the foregoing metals; a polymer; ceramics; glass; a composite comprising polymer and fiberglass; quartz; silicon; or a combination of two or more thereof.

22. The process of claim 4 wherein the capture structure comprises wire mesh.

23. The process of claim 4 wherein the capture structure comprises one or more of inverted cones, liquid-nonwetting porous structure, liquid-wetting porous structure, perforated foil, and fibers.

24. The process of claim 2 wherein the wicking region comprises a wick.

25. The process of claim 24 wherein the wick comprises one or more of sintered metal, metal screen, metal foam, and polymer fibers.

26. The process of claim 2 wherein the wicking region comprises a wicking surface.

27. The process of claim 26 wherein the wicking surface comprises grooves in one or more interior walls of the liquid channel.

28. A process for distilling a fluid mixture in a microchannel distillation unit, the microchannel distillation unit comprising a plurality of microchannel distillation sections, the fluid mixture comprising a more volatile component and a less volatile component, the process comprising:

flowing a vapor phase of the fluid mixture in a first microchannel distillation section in contact with a liquid phase of the fluid mixture, part of the more volatile component transferring from the liquid phase to the vapor phase to form a more volatile component rich vapor phase, part of the less volatile component transferring from the vapor phase to the liquid phase to form a less volatile component rich liquid phase;

separating the more volatile component rich vapor phase from the less volatile component rich liquid phase;

flowing the less volatile component rich liquid phase to another microchannel distillation section upstream from the first microchannel distillation section; and flowing the more volatile rich vapor phase to another microchannel distillation section downstream from the first microchannel distillation section;

wherein each microchannel distillation section comprises at least one process microchannel and at least one adjacent liquid channel, the liquid channel comprising a wicking region, the wicking region comprising a wicking surface, the wicking surface comprising grooves in one or more interior walls of the liquid channel; and wherein the grooves are aligned parallel to the direction of flow of the vapor phase in the process microchannel.

29. A process for distilling a fluid mixture in a microchannel distillation unit, the microchannel distillation unit comprising a plurality of microchannel distillation sections, the fluid mixture comprising a more volatile component and a less volatile component, the process comprising:

flowing a vapor phase of the fluid mixture in a first microchannel distillation section in contact with a liquid phase of the fluid mixture, part of the more volatile component transferring from the liquid phase to the vapor phase to form a more volatile component rich vapor phase, part of the less volatile component transferring from the vapor phase to the liquid phase to form a less volatile component rich liquid phase;

separating the more volatile component rich vapor phase from the less volatile component rich liquid phase;

flowing the less volatile component rich liquid phase to another microchannel distillation section upstream from the first microchannel distillation section; and flowing the more volatile rich vapor phase to another microchannel distillation section downstream from the first microchannel distillation section;

wherein each microchannel distillation section comprises at least one process microchannel and at least one adjacent liquid channel, the liquid channel comprising a wicking region, the wicking region comprising a wicking surface, the wicking surface comprising grooves in one or more interior walls of the liquid channel; and wherein the grooves are aligned tangentially to the direction of flow of the vapor phase in the process microchannel.

30. The process of claim 27 wherein the grooves provide a flow path for the liquid phase to the another microchannel distillation section.

31. The process of claim 1 wherein the flow fo the liquid phase is driven by gravitational forces.

32. The process of claim 1 wherein the flow of the liquid phase is driven by gravitational force and/or a pressure differential.

33. The process of claim 1 wherein the fluid mixture comprises ethane and ethylene.

34. The process of claim 1 wherein the fluid mixture comprises styrene and ethylbenzene.

35. The process of claim 1 wherein the fluid mixture comprises oxygen and nitrogen.

36. The process of claim 1 wherein the fluid mixture comprises cycohexane and cyclohexanol or cyclohexanone.

37. The process of claim 1 wherein the fluid mixture comprises isobutane.

38. The process of claim 1 wherein the fluid mixture comprises naptha.

39. The process of claim 3 wherein the heat exchanger comprises at least one heat exchange channel and an endothermic or exothermic process is conducted in the heat exchange channel.

40. The process of claim 39 wherein the exothermic process comprises a water-gas shift reaction, a methanol synthesis reaction or an ammonia synthesis reaction.

41. The process of claim 39 wherein the endothermic reaction comprises a steam reforming process or dehydrogenation process.

42. The process of claim 3 wherein the heat exchanger comprises at least one heat exchange channel, and a heat exchange fluid flows through the heat exchange channel.

43. The process of claim 42 wherein the heat exchange fluid undergoes a phase change in the heat exchange channel.

44. The process of claim 42 wherein the heat exchange fluid undergoes partial boiling in the heat exchange channel.

45. The process of claim 1 wherein the microchannel distillation sections have adjacent heat exchange channel zones, a heat exchange fluid flows in the heat exchange channel zones, the heat exchange fluid undergoing partial boiling in the heat exchange channel zones, the pressure of the heat exchange fluid in each of the heat exchange channel zones being different.

46. The process of claim 1 wherein the microchannel distillation sections have adjacent heat exchange channel zones, a heat exchange fluid flows in the heat exchange channel zones, the heat exchange fluid undergoing partial boiling in the heat exchange channel zones, the temperature in each microchannel distillation section being different.

47. The process of claim 10 wherein the vapor phase flows through the process microchannel in a first direction, and a heat exchange fluid flows through the heat exchange channel in a second direction, the second direction being co-current, cross-current or counter-current relative to the first direction.

48. The process of claim 10 wherein a heat exchange fluid flows through the heat exchange channel, the heat exchange fluid comprising one or more of air, steam, liquid water, carbon dioxide, gaseous nitrogen, liquid nitrogen, a gaseous hydrocarbon or a liquid hydrocarbon.

49. The process of claim 3 wherein the heat exchanger comprises an electric heating element, resistance heater and/or non-fluid cooling element.

50. The process of claim 10 wherein the gauge pressure within the microchannel distillation sections is in the range from about 30 to about 100 atmospheres, and a heat exchange fluid flows in the heat exchange channel, the temperature of the heat exchange fluid being in the range from about −30 to about 200° C.

51. A process for distilling a fluid mixture in a microchannel distillation unit, the microchannel distillation unit comprising a process microchannel and an adjacent liquid channel, the fluid mixture comprising a more volatile component and a less volatile component, the process comprising:

flowing a vapor phase of the fluid mixture in one direction through the process microchannel, the process microchannel comprising a plurality of microchannel distillation sections, each microchannel distillation section comprising an internal space for permitting vapor flow, an interior wall, a capture structure, a liquid inlet and a liquid outlet, the capture structure and the liquid outlet being downstream from the liquid inlet, the interior wall extending from the liquid inlet to the liquid outlet, the capture structure being suitable for capturing liquid and permitting vapor to flow through it, the liquid outlet being suitable for permitting the flow of the liquid from the capture structure through the liquid outlet into the liquid channel, the liquid inlet being suitable for permitting liquid to flow from the liquid channel into the process microchannel;

flowing a liquid phase of the fluid mixture through the liquid channel in a direction opposite to the direction of flow of the vapor phase in the process microchannel, the liquid channel including a wicking region, the liquid phase flowing through the wicking region;

the liquid phase flowing from the liquid channel through the liquid inlet in a first microchannel distillation section of the process microchannel and flowing as a thin film along the interior wall to the capture structure within the first microchannel distillation section, the vapor phase flowing through the first microchannel distillation section in contact with the liquid phase flowing along the interior wall, part of the more volatile component transferring from the liquid phase to the vapor phase to form a more volatile component rich vapor phase, part of the less volatile component transferring from the vapor phase to the liquid phase to form a less volatile component rich liquid phase, the less volatile component rich liquid phase contacting the capture structure and flowing from the capture structure through the liquid outlet of the first microchannel distillation section into the liquid channel, the more volatile component rich vapor phase flowing through the capture structure of the first microchannel distillation section.

52. The process of claim 51 wherein at least part of the more volatile component rich vapor phase is condensed and withdrawn from the microchannel distillation unit.

53. The process of claim 52 wherein the more volatile component rich vapor phase is condensed in a microchannel condenser.

54. The process of claim 51 wherein at least part of the more volatile component rich vapor phase is condensed and flows into the liquid channel.

55. The process of claim 54 wherein the more volatile component rich vapor phase is condensed in a microchannel condenser.

56. The process of claim 51 wherein at least part of the less volatile component rich liquid phase is withdrawn from the microchannel distillation unit.

57. The process of claim 51 wherein at least part of the less volatile component rich liquid phase is vaporized and flows into the process microchannel.

58. The process of claim 57 wherein the less volatile component rich liquid phase is vaporized in a microchannel reboiler.

59. The process of claim 1 wherein the fluid mixture comprises natural gas, the fluid mixture flows through a series of microchannel distillation units to remove water, butanes and/or butylenes, propanes and/or propylene, and ethane and/or ethylene, from the fluid mixture.

60. A process for separating ethylene from a fluid mixture comprising ethylene and ethane in a distillation unit comprising a plurality of microchannel distillation sections, the process comprising: contacting a vapor phase of the fluid mixture with a liquid phase of the fluid mixture in each of the microchannel distillation sections, progressively enriching the vapor phase with ethylene to form an ethylene enriched vapor phase, and separating the ethylene enriched vapor phase from the distillation unit, the distillation unit having a height of up to about 20 meters, the separated ethylene enriched vapor phase having an ethylene content of at least about 95% by volume.

61. The process of claim 60 wherein the distillation unit has a height of up to about 3 meters.

62. The process of claim 60 wherein the ethylene enriched vapor phase has an ethylene content of at least about 99% by volume.

63. A process for distilling a fluid mixture in a distillation apparatus comprising a plurality of microchannel distillation units, each microchannel distillation unit comprising a plurality of microchannel distillation sections, each microchannel distillation section comprising a liquid inlet and liquid outlet and a vapor inlet and vapor outlet, the fluid mixture comprising a more volatile component and a less volatile component, the process comprising:

flowing a vapor phase of the fluid mixture in the first microchannel distillation section of at least one microchannel distillation unit in contact with a liquid phase of the fluid mixture, part of the more volatile component transferring from the liquid phase to the vapor phase to form a more volatile component rich vapor phase, part of the less volatile component transferring from the vapor phase to the liquid phase to form a less volatile component rich liquid phase;

separating the more volatile component rich vapor phase from the less volatile component rich liquid phase;

flowing the less volatile component rich liquid phase to the another microchannel distillation section in the microchannel distillation unit upstream from the first microchannel distillation section; and flowing the more volatile rich vapor phase to the another microchannel distillation section in the microchannel distillation unit downstream from the first microchannel distillation section.

64. The process of claim 63 wherein the distillation process is conducted in all of the microchannel distillation units in the distillation apparatus.

65. A process for distilling a fluid mixture in a distillation apparatus comprising a plurality of microchannel distillation units, each microchannel distillation unit comprising a plurality of microchannel distillation sections, the fluid mixture comprising a more volatile component and a less volatile component, the process comprising:

flowing a vapor phase of the fluid mixture in a first microchannel distillation section of at least one microchannel distillation unit in contact with a liquid phase of the fluid mixture, part of the more volatile component transferring from the liquid phase to the vapor phase to form a more volatile component rich vapor phase, part of the less volatile component transferring from the vapor phase to the liquid phase to form a less volatile component rich liquid phase;

separating the more volatile component rich vapor phase from the less volatile component rich liquid phase;

flowing the less volatile component rich liquid phase to another microchannel distillation section in the microchannel distillation unit upstream from the first microchannel distillation section;

flowing the more volatile rich vapor phase to another microchannel distillation section in the microchannel distillation unit downstream from the first microchannel distillation section; and wherein the distillation process is conducted in some but not all of the microchannel distillation units in the distillation apparatus.

66. A microchannel distillation unit, comprising: a process microchannel and a liquid channel; the liquid channel being adjacent to the process microchannel, the liquid channel comprising a wicking region; the process microchannel comprising a plurality of microchannel distillation sections connected in series, each microchannel distillation section comprising an internal space for permitting vapor flow, an interior wall for permitting liquid to flow as a thin film along the interior wall, a capture structure for capturing liquid and permitting vapor to flow through it, a liquid outlet for permitting liquid to flow from the capture structure into the liquid channel, and a liquid inlet for permitting liquid to flow from the liquid channel into the process microchannel.

67. The microchannel distillation unit of claim 66 wherein the microchannel distillation unit further comprises a microchannel condenser for condensing vapor.

68. The microchannel distillation unit of claim 66 wherein the microchannel distillation unit further comprises a microchannel reboiler for vaporizing liquid.

69. A microchannel distillation unit, comprising: a process microchannel and a liquid channel; the liquid channel being adjacent to the process microchannel, the liquid channel comprising a wicking region; the process microchannel comprising a plurality of microchannel distillation sections, each microchannel distillation section comprising an internal space for permitting vapor flow, an interior wall for permitting liquid to flow as a thin film along the interior wall, a capture structure for capturing liquid and permitting vapor to flow through it, a liquid outlet for permitting liquid to flow from the capture structure into the liquid channel, and a liquid inlet for permitting liquid to flow from the liquid channel into the process microchannel; and wherein the microchannel distillation unit further comprises a heat exchange channel adjacent to the liquid channel, the process microchannel, or both the liquid channel and the process microchannel.

70. The microchannel distillation unit of claim 66 wherein the process microchannel has an internal dimension of width or height of up to about 10 mm.

71. The microchannel distillation unit of claim 66 wherein the process microchannel has an internal dimension of width or height of up to about 2 mm.

72. The microchannel distillation unit of claim 66 wherein the process microchannel is made of a material comprising: steel; monel; inconel; aluminum; titanium; nickel; copper; brass; an alloy of any of the foregoing metals; a polymer; ceramics; glass; a composite comprising a polymer and fiberglass; quartz; silicon; silicon carbide; boron carbide; metal carbide; silicon nitride; boron nitride; metal nitride; or a combination of two or more thereof.

73. The microchannel distillation unit of claim 66 wherein the liquid channel comprises a microchannel.

74. The microchannel distillation unit of claim 66 wherein the liquid channel has an internal dimension of width or height of up to about 10 mm.

75. The microchannel distillation unit of claim 66 wherein the liquid channel has an internal dimension of width or height of up to about 2 mm.

76. The microchannel distillation unit of claim 66 wherein the liquid channel is made of a material comprising: steel; monel; inconel; aluminum; titanium; nickel; copper; brass; an alloy of any of the foregoing metals; a polymer; ceramics; glass; a composite comprising polymer and fiberglass; quartz; silicon; silicon carbide; boron carbide; metal carbide; silicon nitride; boron nitride; metal nitride; or a combination of two or more thereof.

77. The microchannel distillation unit of claim 69 wherein the heat exchange channel has an internal dimension of width or height of up to about 10 mm.

78. The microchannel distillation unit of claim 69 wherein the heat exchange channel has an internal dimension of width or height of up to about 2 mm.

79. The microchannel distillation unit of claim 69 wherein the heat exchange channel is made of a material comprising: steel; monel; inconel; aluminum; titanium; nickel; copper; brass; an alloy of any of the foregoing metals; a polymer; ceramics; glass; a composite comprising polymer and fiberglass; quartz; silicon; silicon carbide; boron carbide; metal carbide; silicon nitride; boron nitride; metal nitride; or a combination of two or more thereof.

80. The microchannel distillation unit of claim 66 wherein the capture structure comprises wire mesh.

81. The microchannel distillation unit of claim 66 wherein the capture structure comprises one or more of inverted cones, liquid-nonwetting porous structure, liquid-wetting porous structure, perforated foil, and fibers.

82. The microchannel distillation unit of claim 66 wherein the capture structure comprises one or more of sintered metal, metal screen, metal foam, and polymer fibers.

83. The microchannel distillation unit of claim 66 wherein the wicking region comprises a wick.

84. The microchannel distillation unit of claim 66 wherein the wicking region comprises a wicking surface.

85. The microchannel distillation unit of claim 66 wherein the microchannel distillation unit is formed using sheets of material with portions removed that allow flow passage.

86. The microchannel distillation unit of claim 66 wherein the microchannel distillation unit is formed using a stack of sheets to form an integrated microchannel distillation unit.

87. The microchannel distillation unit of claim 66 wherein the microchannel distillation unit is assembled using a combination of sheets and partial sheets.

88. A microchannel distillation unit, comprising: a liquid channel, a first process microchannel, a second process microchannel, a first vapor channel, a second vapor channel, a third vapor channel, a vapor inlet and a vapor outlet, the first process microchannel and the second process microchannel being adjacent to the liquid channel, the liquid channel comprising a wicking region, part of the wicking region forming a wall of the first process microchannel and a wall of the second process microchannel, the first vapor channel being adjacent to the first process microchannel, the third vapor channel being adjacent to the second process microchannel, the second vapor channel being adjacent to the first and third vapor channels, the first and third vapor channels being positioned between the first and second process microchannels and the second vapor channel.

89. A process for distilling a fluid mixture in a microchannel distillation unit, the microchannel distillation unit comprising a plurality of microchannel distillation sections, the fluid mixture comprising a more volatile component and a less volatile component, the process comprising:

flowing a vapor phase of the fluid mixture in a first microchannel distillation section in contact with a liquid phase of the fluid mixture, the first microchannel distillation section comprising at least one process microchannel and at least one liquid channel, the vapor phase and part of the liquid phase flowing in the process microchannel in a first direction, part of the liquid phase flowing in the liquid channel in a second direction, the first direction being counter-current to the second direction, part of the more volatile component transferring from the liquid phase to the vapor phase to form a more volatile component rich vapor phase, part of the less volatile component transferring from the vapor phase to the liquid phase to form a less volatile component rich liquid phase;

separating the more volatile component rich vapor phase from the less volatile component rich liquid phase;

flowing the less volatile component rich liquid phase to another microchannel distillation section upstream from the first microchannel distillation section; and flowing the more volatile rich vapor phase to another microchannel distillation section downstream from the first microchannel distillation section.

90. A process for distilling a fluid mixture in a microchannel distillation unit, the microchannel distillation unit comprising a plurality of microchannel distillation sections, the fluid mixture comprising a more volatile component and a less volatile component, the process comprising:

flowing a vapor phase of the fluid mixture in a first microchannel distillation section in contact with a liquid phase of the fluid mixture, part of the more volatile component transferring from the liquid phase to the vapor phase to form a more volatile component rich vapor phase, part of the less volatile component transferring from the vapor phase to the liquid phase to form a less volatile component rich liquid phase;

separating the more volatile component rich vapor phase from the less volatile component rich liquid phase;

flowing the less volatile component rich liquid phase to another microchannel distillation section upstream from the first microchannel distillation section; and flowing the more volatile rich vapor phase to another microchannel distillation section downstream from the first microchannel distillation section;

wherein for each microchannel distillation section the process microchannel comprises a liquid inlet for permitting liquid to flow into the process microchannel, a liquid outlet for permitting liquid to flow out of the process microchannel, an interior wall extending from the liquid entrance to the liquid exit, and a capture structure, the liquid outlet being downstream from the liquid inlet; and wherein the microchannel distillation unit further comprises a first supplemental vapor channel and a second supplemental vapor channel, each microchannel distillation section further comprising a supplemental vapor inlet and a supplemental vapor outlet, part of the vapor phase flowing from the first supplemental vapor channel through the supplemental vapor inlet into the microchannel distillation section, through the microchannel distillation section in contact with the liquid phase, and through the supplemental vapor outlet to the second supplemental vapor channel.

91. A microchannel distillation unit, comprising: a process microchannel and a liquid channel; the liquid channel being adjacent to the process microchannel, the liquid channel comprising a wicking region; the process microchannel comprising a plurality of microchannel distillation sections, each microchannel distillation section comprising an internal space for permitting vapor flow, an interior wall for permitting liquid to flow as a thin film along the interior wall, a capture structure for capturing liquid and permitting vapor to flow through it, a liquid outlet for permitting liquid to flow from the capture structure into the liquid channel, and a liquid inlet for permitting liquid to flow from the liquid channel into the process microchannel;

wherein the microchannel distillation unit further comprises a first supplemental vapor channel and a second supplemental vapor channel, and each microchannel distillation section further comprises a supplemental vapor inlet and a supplemental vapor outlet, the first supplemental vapor channel and the supplemental vapor inlet being suitable for permitting vapor to flow from the first supplemental vapor channel into the microchannel distillation section, the second supplemental vapor channel and the supplemental vapor outlet being suitable for permitting vapor to flow from the microchannel distillation section to second supplemental vapor channel.

* * * * *

UNITED STATES PATENT AND TRADEMARK OFFICE
CERTIFICATE OF CORRECTION

| | |
|---|---|
| PATENT NO. | : 7,305,850 B2 |
| APPLICATION NO. | : 10/898687 |
| DATED | : December 11, 2007 |
| INVENTOR(S) | : Tonkovich et al. |

It is certified that error appears in the above-identified patent and that said Letters Patent is hereby corrected as shown below:

Column 32, line 55, replace "each" with --the plurality of microchannel distillation sections comprising a first microchannel distillation section, another microchannel distillation section upstream from the first microchannel distillation section, and another microchannel distillation section downstream from the first microchannel distillation section, the first--.

Column 39, line 50, replace "each" with --the plurality of microchannel distillation sections comprising a first microchannel distillation section, another microchannel distillation section upstream from the first microchannel distillation section, and another microchannel distillation section downstream from the first microchannel distillation section, the first--.

Signed and Sealed this

Twentieth Day of May, 2008

JON W. DUDAS
*Director of the United States Patent and Trademark Office*